(12) United States Patent
Yamamoto et al.

(10) Patent No.: US 11,291,388 B2
(45) Date of Patent: Apr. 5, 2022

(54) EXERCISE SUPPORT DEVICE, EXERCISE SUPPORT METHOD AND STORAGE MEDIUM

(71) Applicant: CASIO COMPUTER CO., LTD., Tokyo (JP)

(72) Inventors: Ryohei Yamamoto, Tachikawa (JP); Tomoaki Nagasaka, Koganei (JP)

(73) Assignee: CASIO COMPUTER CO., LTD., Tokyo (JP)

(*) Notice: Subject to any disclaimer, the term of this patent is extended or adjusted under 35 U.S.C. 154(b) by 1402 days.

(21) Appl. No.: 14/855,193

(22) Filed: Sep. 15, 2015

(65) Prior Publication Data

US 2016/0081612 A1    Mar. 24, 2016

(30) Foreign Application Priority Data

Sep. 19, 2014  (JP) .............................. JP2014-191814

(51) Int. Cl.
*A61B 5/11* (2006.01)
*A61B 5/00* (2006.01)

(52) U.S. Cl.
CPC ............. *A61B 5/112* (2013.01); *A61B 5/1118* (2013.01); *A61B 5/1121* (2013.01); *A61B 5/6823* (2013.01); *A61B 5/74* (2013.01); *A61B 2503/10* (2013.01); *A61B 2562/0219* (2013.01)

(58) Field of Classification Search
CPC ..... A61B 5/112; A61B 5/1118; A61B 5/1121; A61B 5/6823; A61B 5/74; A61B 2562/0219; A61B 2503/10
See application file for complete search history.

(56) References Cited

U.S. PATENT DOCUMENTS

| | | | | |
|---|---|---|---|---|
| 6,571,200 B1* | 5/2003 | Mault | ................... | A61B 5/0002 |
| | | | | 702/182 |
| 2007/0208544 A1* | 9/2007 | Kulach | ................. | A61B 5/1112 |
| | | | | 702/189 |
| 2008/0214360 A1* | 9/2008 | Stirling | ................ | A61B 5/1038 |
| | | | | 482/9 |
| 2009/0043531 A1* | 2/2009 | Kahn | ..................... | G16H 40/63 |
| | | | | 702/149 |

(Continued)

FOREIGN PATENT DOCUMENTS

JP         10325735 A      12/1998

*Primary Examiner* — Rene T Towa
(74) *Attorney, Agent, or Firm* — Holtz, Holtz & Volek PC

(57) ABSTRACT

An exercise support device includes a motion sensor that is worn on a user's body and outputs data regarding the motion status of the user's body when the user is performing a moving exercise, and a control section which acquires exercise information regarding the user's exercise status. The control section selects a specific exercise index having relatively strong correlation with a moving speed from exercise indexes acquired from the data outputted when the user moves on a movement section plural times at moving speeds different from each other, acquires a coefficient that is used in an approximate expression which represents the specific exercise index and is a linear function including the moving speed as a variable and the coefficient, and acquires the exercise information based on the specific exercise index and the coefficient when the user moves by the moving exercise.

15 Claims, 14 Drawing Sheets

(56) References Cited

U.S. PATENT DOCUMENTS

| | | | |
|---|---|---|---|
| 2013/0274587 A1* | 10/2013 | Coza | A61B 5/6804 600/409 |
| 2014/0114561 A1* | 4/2014 | Pakzad | G01C 21/206 701/410 |
| 2014/0156215 A1* | 6/2014 | Eastman | A61B 5/112 702/141 |
| 2015/0342476 A1* | 12/2015 | Takakura | A61B 5/6831 600/509 |

* cited by examiner

EXAMPLE OF EXPLANATION DISPLAY

FEATURES OF YOUR WAY OF RUNNING WILL NOW BE LEARNED BY MEASUREMENT DEVICE.
1. SET MOVEMENT SECTION OF ABOUT 50M, AND RUN IN THAT SECTION SLOWLY.
2. NEXT, RUN IN SAME MOVEMENT SECTION AGAIN AT NORMAL SPEED.
3. THEN, RUN IN SAME MOVEMENT SECTION AGAIN AT RELATIVELY FASTER SPEED.

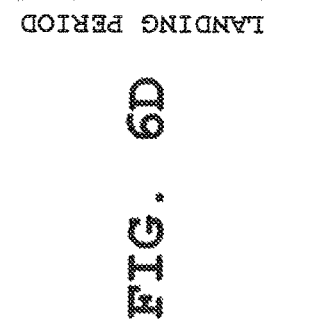
RUNNER A
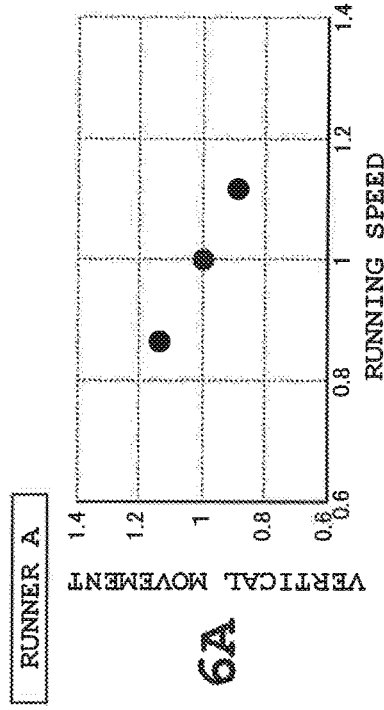
FIG. 6A  VERTICAL MOVEMENT
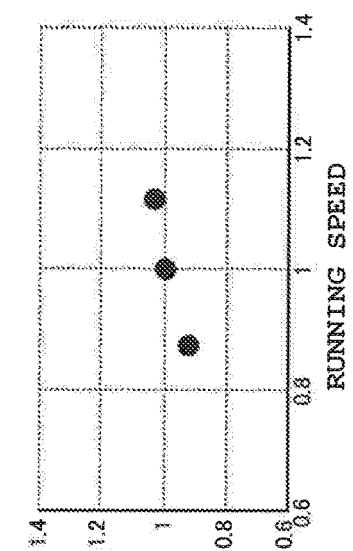
FIG. 6D  LANDING PERIOD
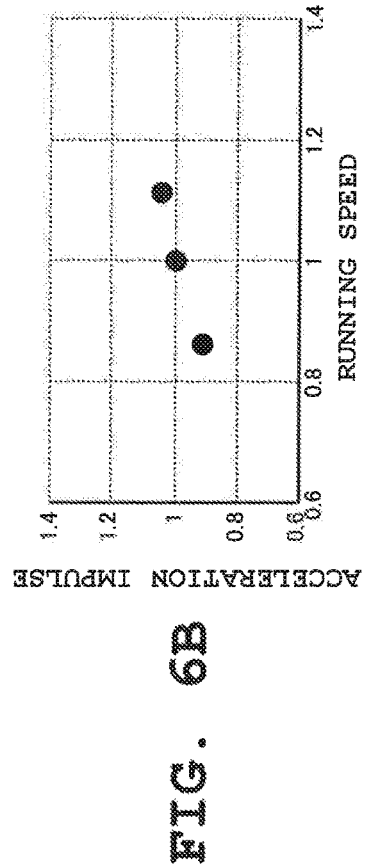
FIG. 6B  ACCELERATION IMPULSE
FIG. 6C  FORWARD DIRECTION IMPULSE
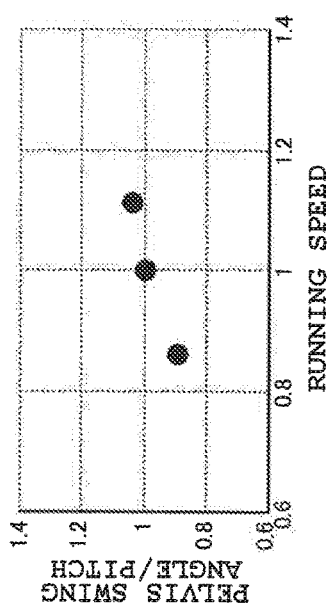
FIG. 6E  PELVIS SWING ANGLE/YAW
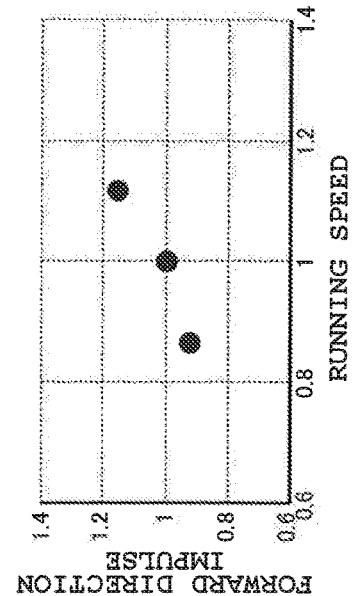
FIG. 6F  PELVIS SWING ANGLE/PITCH

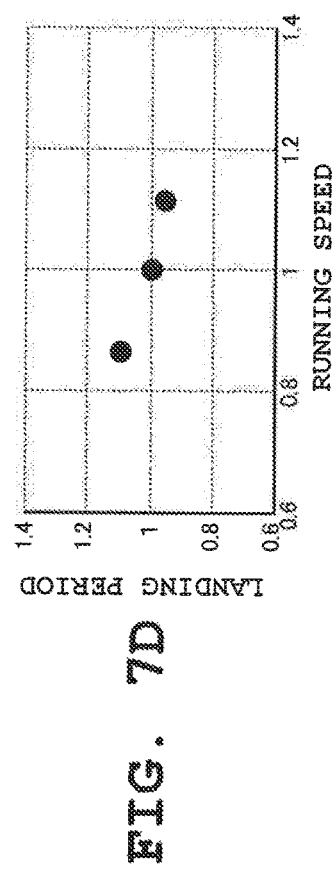
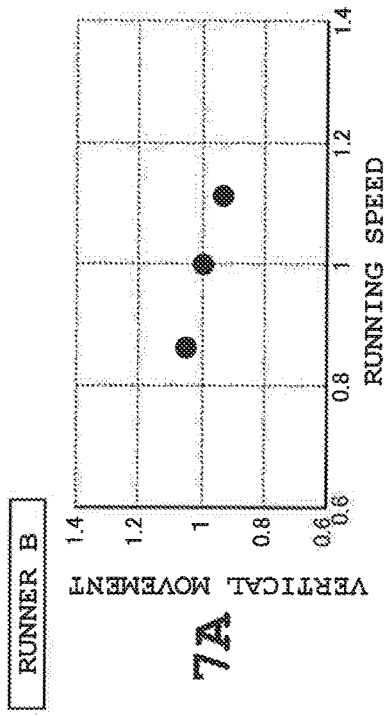
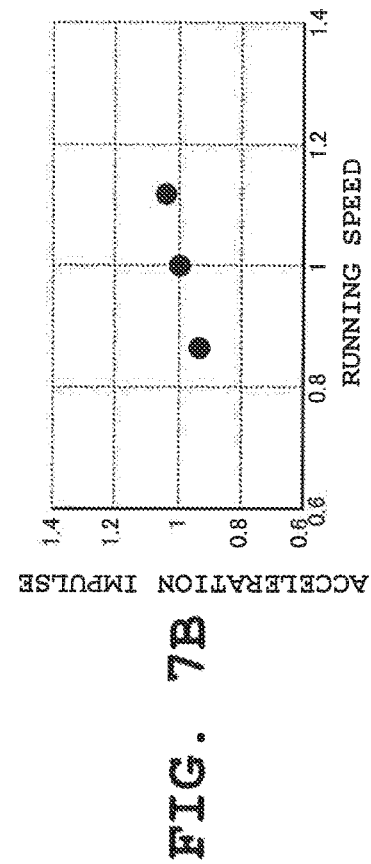
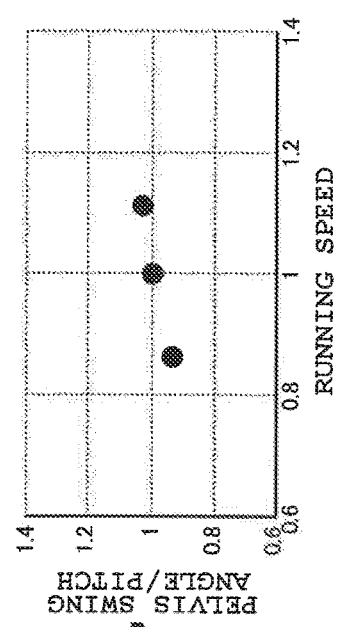
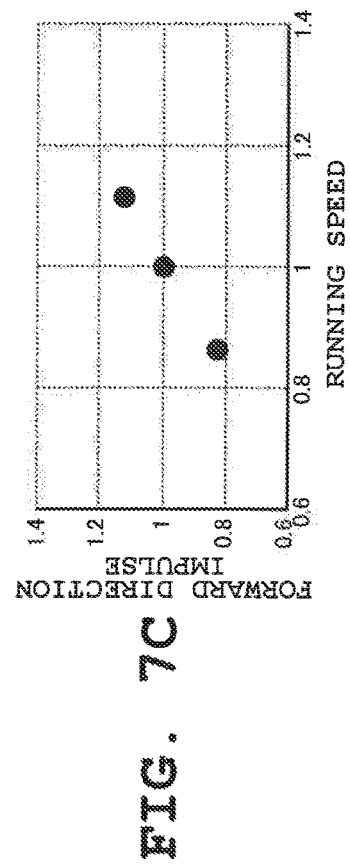
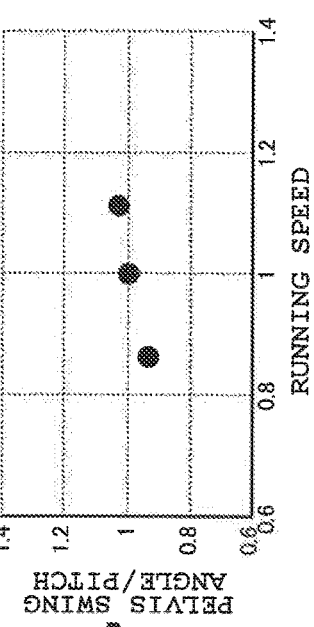

EXERCISE SUPPORT DEVICE, EXERCISE SUPPORT METHOD AND STORAGE MEDIUM

CROSS-REFERENCE TO RELATED APPLICATION

This application is based upon and claims the benefit of priority from the prior Japanese Patent Application No. 2014-191814, filed Sep. 19, 2014, the entire contents of which are incorporated herein by reference.

BACKGROUND OF THE INVENTION

1. Field of the Invention

The present invention relates to an exercise support device, an exercise support method, and a storage medium by which the motion status (exercise status) of a human body during exercise is grasped so that the user can judge and improve the exercise status.

2. Description of the Related Art

In recent years, because of rising health consciousness, more and more people are performing daily exercises, such as running, walking, and cycling, to maintain their wellness or improve their health conditions.

In addition, an increasing number of people are aiming to participate in a race such as a marathon race through these daily exercises. These people are very conscious of and interested in measuring and recording various biological and exercise information by numerical values and data so as to grasp their own health conditions and exercise statuses. The people aiming to participate in a race have an objective of achieving a successful record in the race, and therefore are very conscious of and interested in efficient and effective training methods.

As a method for grasping a health condition and an exercise status, a method is effective in which specific easily-understandable information is generated based on numerical values and data measured during exercise and visually presented. For example, in a case where the status and the form of running are quantitatively evaluated, it is effective to present information such as a running speed, a stride, and a pitch. Here, as a method for measuring a running speed and a stride in a running exercise or a marathon race, for example, a method using positioning data and reception signals by GPS (Global Positioning System) is known. For example, Japanese Patent Application Laid-Open (Kokai) Publication No. 10-325735 describes a technique where a stride per step is calculated based on a distance calculated based on the speed of a human body measured from the Doppler frequency of a carrier wave received by a GPS reception device worn on the human body, and the number of steps calculated based on vibration displacement detected by an acceleration sensor, and then the movement distance and the movement speed are calculated based on the stride which is updated by a GPS radio wave being periodically received, and the added number of steps.

The above-described patent application discloses a method where the movement speed, the movement distance, and the stride of a human body are calculated based on positioning data acquired by GPS. In this method, in order to keep the correctness and the accuracy of positioning data, radio waves from a number of GPS satellites are required to be received. However, a moving speed, a movement distance, a stride, and the like cannot be accurately calculated in a place where radio waves from GPS satellites are difficult or impossible to receive, such as indoor areas and places between buildings. In this case, the exercise status cannot be accurately grasped, and therefore the improvement thereof cannot be appropriately supported.

SUMMARY OF THE INVENTION

The present invention has an advantage of providing an exercise support device, an exercise support method, and a storage medium by which the exercise status of a human body is accurately grasped based on data regarding the motion status of the human body outputted from a motion sensor worn on the human body, and utilized for supporting the improvement of the exercise status.

In accordance with one aspect of the present invention, there is provided an exercise support device comprising: a motion sensor which is worn on a body of a user, and outputs sensor data related to a motion status of the body of the user when the user is performing a moving exercise; and a control section which acquires exercise information regarding an exercise status of the user based on the sensor data, wherein the control section (i) acquires a plurality of exercise indexes from the sensor data when the user moves on a movement section plural times at moving speeds different from each other by the moving exercise, (ii) selects a specific exercise index having relatively strong correlation with a moving speed from the plurality of exercise indexes, (iii) acquires a coefficient that is used in an approximate expression which represents the specific exercise index and is a linear function including the moving speed as a variable and the coefficient, and (iv) acquires the exercise information based on the specific exercise index and the coefficient when the user moves on a movement route different from the movement section by the moving exercise.

In accordance with another aspect of the present invention, there is provided an exercise support method comprising: a step of acquiring a plurality of exercise indexes from sensor data outputted from a motion sensor worn on a body of a user when the user moves on a movement section plural times at moving speeds different from each other by a moving exercise; a step of selecting a specific exercise index having relatively strong correlation with a moving speed from the plurality of exercise indexes; a step of acquiring a coefficient that is used in an approximate expression which represents the specific exercise index and is a linear function including the moving speed as a variable and the coefficient; and a step of acquiring exercise information regarding an exercise status of the user based on the specific exercise index and the coefficient when the user moves on a movement route different from the movement section by the moving exercise.

In accordance with another aspect of the present invention, there is provided a non-transitory computer-readable storage medium having an exercise support program stored thereon that is executable by a computer to actualize functions comprising: processing for acquiring a plurality of exercise indexes from sensor data outputted from a motion sensor worn on a body of a user when the user moves on a movement section plural times at moving speeds different from each other by a moving exercise; processing for selecting a specific exercise index having relatively strong correlation with a moving speed from the plurality of exercise indexes; processing for acquiring a coefficient that is used in an approximate expression which represents the specific exercise index and is a linear function including the moving speed as a variable and the coefficient; and processing for acquiring exercise information regarding an exercise status of the user based on the specific exercise index and the coefficient when the user is moving on a movement route different from the movement section by the moving exercise.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 6A to FIG. 6F are graphs of examples (correlation between the moving speed and respective exercise indexes of runner A) of measurement in the individual characteristic evaluation mode according to the embodiment;

FIG. 7A to FIG. 7F are graphs of examples (correlation between the moving speed and respective exercise indexes of runner B) of measurement in the individual characteristic evaluation mode according to the embodiment;

DETAILED DESCRIPTION OF THE PREFERRED EMBODIMENTS

Hereinafter, an exercise support device and an exercise support method according to the present invention are described in detail with reference to the drawings.

Note that, in the following description of the embodiments a case is exemplified where a moving speed, a stride, a pitch, and the like when a user is running are estimated based on sensor data collected while the user is running around a running track on an athletic field or the like or running a predetermined running course or a marathon course, and information based thereon are provided to the user. However, the present invention is not limited to this case where the user moves by running, and can also be applied in a case where the user moves by walking.

<Exercise Support Device>

Figure 1:
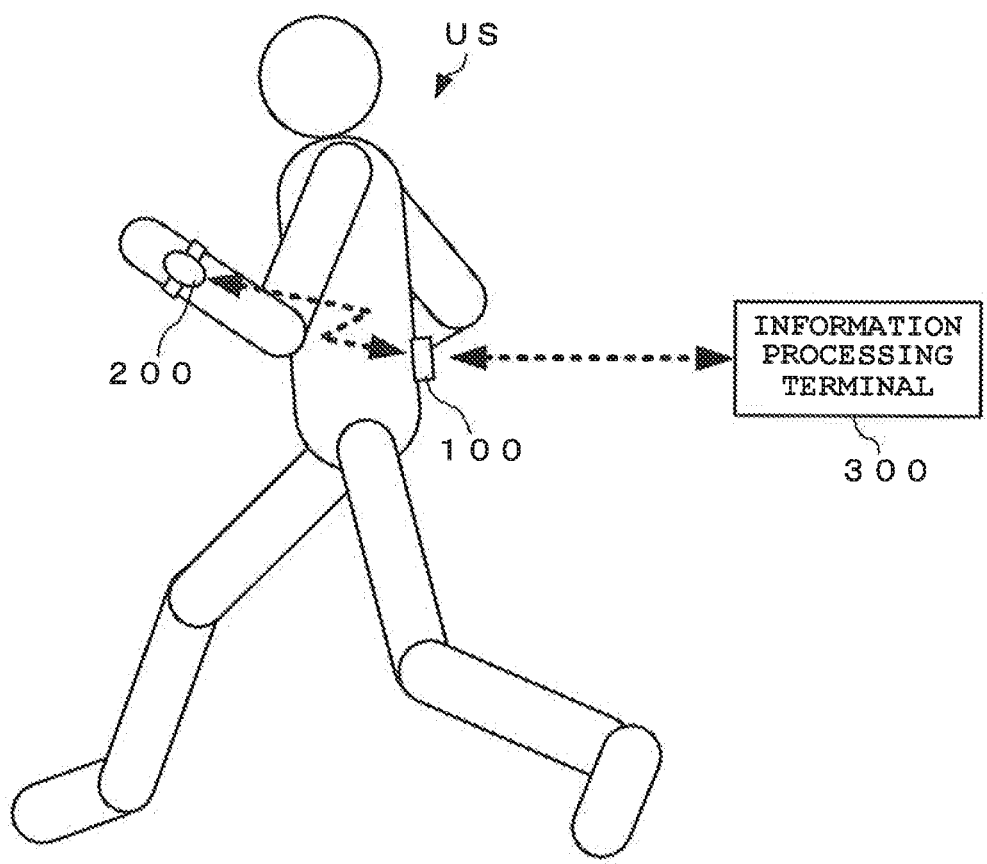
FIG. 1 is a schematic structural diagram of an embodiment of an exercise support device according to the present invention.

FIG. 1 is a schematic structural diagram of an embodiment of an exercise support device according to the present invention.

Figure 2A:
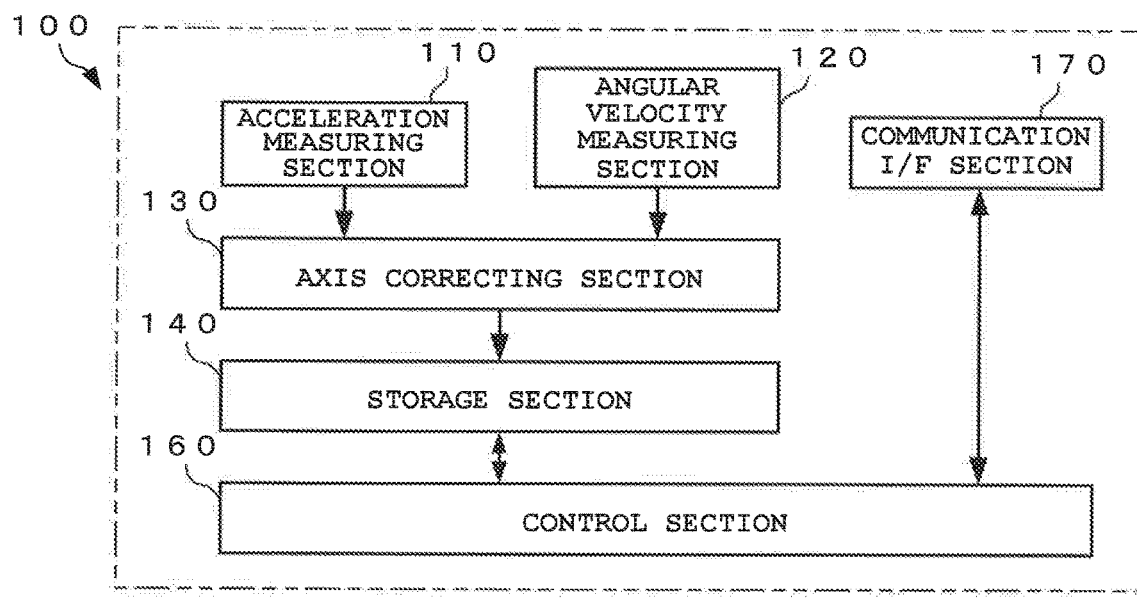
FIG. 2A, FIG. 2B, and FIG. 2C are schematic block diagrams showing each structure applied in the exercise support device according to the embodiment.
Figure 2B:
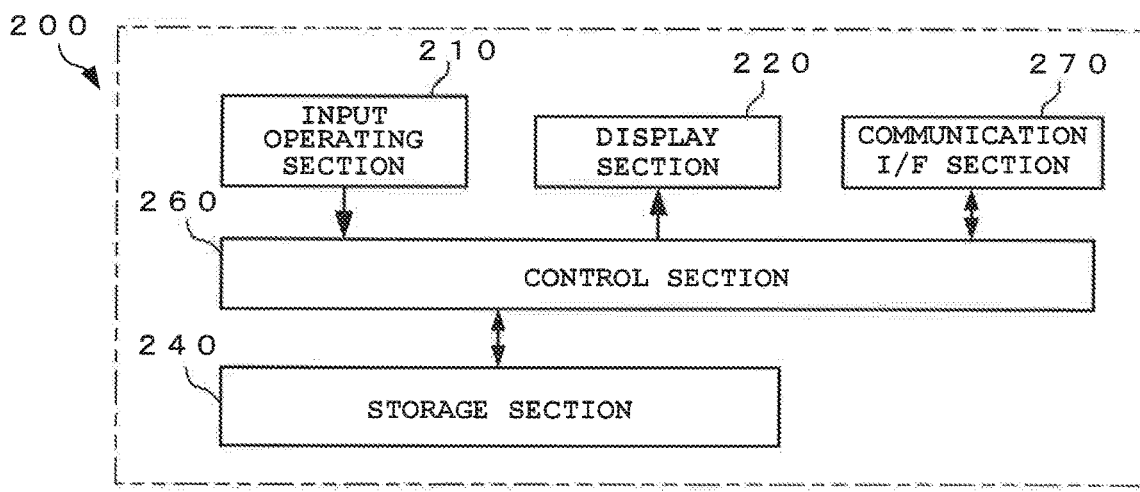
Figure 2C:
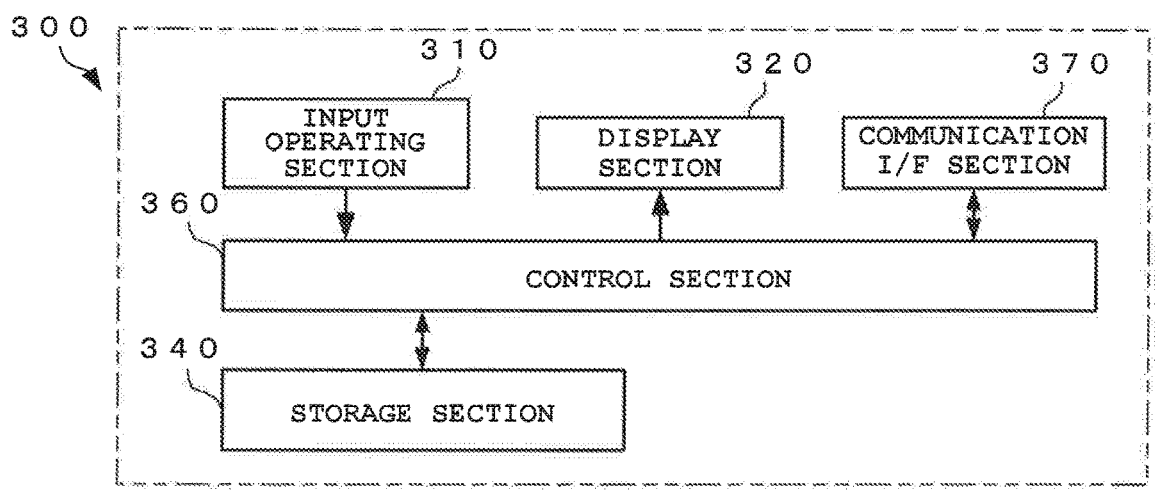

FIG. 2A, FIG. 2B, and FIG. 2C are schematic block diagrams showing each structure applied in the exercise support device according to the present embodiment. Here, FIG. 2A is a schematic block diagram showing the structure of a sensor device that constitutes the exercise support device, FIG. 2B is a schematic block diagram showing the structure of a wrist device that constitutes the exercise support device, and FIG. 2C is a schematic block diagram showing the structure of an information processing terminal that constitutes the exercise support device.

The exercise support device according to the present embodiment of the present invention has, for example, a sensor device 100 that is worn on the lumbar part on the back side of a user US, a control device (hereinafter referred to as a "wrist device") 200 of a wristwatch type or a wristband type that is worn on a wrist or the like of the user US, and an information processing terminal 300 that analyzes a movement trajectory and the like and provides the user with various data regarding an exercise status in a predetermined display form, as depicted in FIG. 1.

The sensor device 100 has functions for collecting, for each predetermined operation mode, sensor data acquired by measuring the motion status of a human body performing a moving exercise involving movements such as a running exercise or a marathon by using a motion sensor (an acceleration measuring section and an angular velocity measuring section), estimating various data regarding the exercise status based on the sensor data, and generating a provisional movement trajectory.

Specifically, the sensor device 100 includes, for example, an acceleration measuring section (a sensor section or a motion sensor) 110, an angular velocity measuring section (a sensor section or a motion sensor) 120, an axis correcting section 130, a storage section 140, a control section (a provisional stride estimating section, a movement trajectory estimating section, an exercise index selecting section, or a traveling direction estimating section) 160, and a communication interface section 170, as depicted in FIG. 2A.

The acceleration measuring section 110 measures the change ratio of the motion speed (acceleration) of the exercising user US. This acceleration measuring section 110, which has a triaxial acceleration sensor, detects acceleration components (acceleration signals) in three axis directions orthogonal to each other, and outputs them as sensor data.

The angular velocity measuring section 120 measures the change of the motion direction (angular velocity) of the exercising user US. This angular velocity measuring section 120, which has a triaxial angular velocity sensor, detects angular velocity components (angular velocity signals) occurred in the rotational directions of rotational motions around the three axes that are orthogonal to each other, and outputs them as sensor data.

The axis correcting section 130 performs axis correction processing on the sensor data (acceleration data and angular velocity data) outputted from the acceleration measuring section 110 and the angular velocity measuring section 120.

Specifically, in general, the lumbar part on the backside of the human body leans forward with respect to the vertical axis indicating the direction of gravity vertical to the ground surface, even in an upright state. Therefore, an axis in the up-and-down direction of the mounted sensor device 100 also leans forward with respect to the vertical axis.

When the user US starts running, the lumbar part further leans forward to cause the axis in the up-and-down direction of the sensor device 100 to further lean forward. As a result, a tilt angle change due to the running motion is further added to the sensor data outputted from the acceleration measuring section 110 and the angular velocity measuring section 120 during the running motion.

Thus, the axis correcting section 130 averages acceleration components for each axis for several cycles of the running motion. By this averaging, components of the acceleration components in the direction of gravity remain, and the direction of gravity is specified based on the remaining components. The axis correcting section 130 corrects the sensor data (acceleration data and angular velocity data) by rotating each of the axes of the acceleration signal and the angular velocity signal such that the up-and-down direction the acceleration data outputted from the acceleration measuring section 110 matches with the specified direction of gravity.

The storage section 140 stores in a predetermined storage area the sensor data (acceleration data and angular velocity data) axially corrected by the axis correcting section 130, various data regarding an exercise status estimated by the control section 160 based on the sensor data, a generated provisional movement trajectory, course data of a race received from the information processing terminal 300 described below, a correction coefficient described below, and the like.

The control section 160 performs predetermined signal processing on the corrected sensor data stored in the storage section 140.

Specifically, based on the corrected sensor data, the control section 160 performs processing for estimating various data such as a pitch, a moving speed (running speed), a stride, and the like during the running, and processing (optimum exercise index selection processing) for selecting a specific exercise index in accordance with individual characteristics (hereinafter referred to as "optimum exercise index") for estimating the above-mentioned various data.

Furthermore, the control section 160 performs processing for generating a provisional movement trajectory during the running based on the corrected sensor data (provisional movement trajectory generation processing).

Note that various signal processing to be performed by the control section 160 will be described further below in detail.

The control section 160 is an arithmetic processing unit having a clocking function, such as a CPU (Central Processing Unit), and executes a predetermined control program based on a predetermined operation clock.

As a result, the control section 160 controls various types of operations, such as a sensing operation by the acceleration measuring section 110 and the angular velocity measuring section 120, an operation of storing and reading various data in and from the storage section 140, and an operation of transmitting and receiving a control signal and various data to and from the wrist device 200 and the information processing terminal 300 via the communication interface section 170, which will be described further below.

The control section 160 further executes a predetermined algorithm program to control the axis correction processing on the sensor data by the axis correcting section 130.

The communication interface section (hereinafter abbreviated as "communication I/F section") 170 receives a control signal transmitted from the wrist device 200 described below, and transfers it to the control section 160, whereby the setting of an operation mode (individual characteristic evaluation mode, training mode, or race mode) in the sensor device 100 and the start and end of a sensing operation by the acceleration measuring section 110 and the angular velocity measuring section 120 are controlled.

Also, the communication I/F section 170 transmits sensor data outputted from the acceleration measuring section 110 and the angular velocity measuring section 120, various data regarding an exercise status estimated by the control section 160, a provisional movement trajectory, and the like to the wrist device 200 and the information processing terminal 300 described below.

Moreover, the information I/F section 170 receives course data in a race and a correction coefficient described below from the information processing terminal 300.

Note that, as a method for transmitting and receiving various signals and data to and from the sensor device 100 and the wrist device 200 in the communication I/F section 170, various types of wireless communication methods such as Bluetooth (registered trademark) and Wi-Fi (Wireless Fidelity (registered trademark)) can be adopted.

As a method for transmitting and receiving various signals and data to and from the sensor device 100 and the information processing terminal 300, various types of wired communication methods such as a method using a USB (Universal Serial Bus) standard communication cable and a method of changing a removable storage medium such as a memory card can also be adopted, in addition to the above-described wireless communication methods.

The wrist device 200 is worn on a part (for example, a wrist) of the body at which the wrist device 200 can be visually recognized by the user US easily. This wrist device 200 is connected to the sensor device 100 by using, for example, a predetermined wireless communication method.

The wrist device 200 has a function for setting an operation mode in the sensor device 100 and a function for displaying various data regarding an exercise status estimated based on sensor data outputted from the sensor device 100 in a form that can be visually recognized by the user US.

Specifically, the wrist device 200 includes, for example, an input operating section 210, a display section 220, a storage section 240, a control section 260, and a communication I/F section 270, as depicted in FIG. 2B.

The input operating section 210 is input means such as a button switch provided on the housing of the wrist device 200 and a touch panel provided on the front surface of the display section 220 described below. This input operating section 210 is used for an input operation for, for example, setting an operation mode in the sensor device 100 and giving an instruction to start or end a sensing operation by the sensor device 100.

The display section 220 displays at least data regarding an input operation in the input operating section 210, various data regarding the exercise status of the user US estimated by the sensor device 100, and the like in a predetermined form.

The storage section 240 stores, in a predetermined storage area, at least various data regarding the exercise status of the user US transmitted from the sensor device 100 via the communication I/F section 270 described below.

The control section 260 is an arithmetic processing unit such as a CPU (Central Processing Unit). By executing a predetermined control program, the control section 260 controls various operations such as an operation of displaying various data on the display section 220, an operation of storing and reading data in and from the storage section 240, and an operation for the communication of the communication I/F section 270 with the sensor device 100.

The communication I/F section 270 transmits, to the sensor device 100, a control signal regarding an operation mode to be set in the sensor device 100 by the input operating section 210, a control signal for giving an instruction to start or end a sensing operation in the sensor device 100, and the like.

Also, the communication I/F section 270 receives various data regarding the exercise status of the user US estimated by the sensor device 100.

Note that, although a control device of a wristwatch type (or a wristband type) which is worn on a wrist of the user US as depicted in FIG. 1 has been described in the present embodiment, the present invention is not limited thereto.

That is, the control device may be accommodated in a pocket or may be worn on an upper arm part. Also, the control device may be in a form of a portable information terminal such as a smartphone, or a dedicated terminal.

The information processing terminal 300 has a function for displaying exercise information for each movement section in association with a map based on sensor data and a provisional movement trajectory transmitted from the sensor device 100 after the end of a moving exercise of the user US and map data acquired by the user US such that the provisional movement trajectory matches with the course in the map.

Here, the information processing terminal 300 may be any terminal as long as it includes a display panel and has a function for executing an exercise support program described below. For example, the information processing terminal 300 may be a notebook-type or desktop-type personal computer, or a portable information terminal such as a smartphone (high-functionality portable telephone) or tablet terminal.

Specifically, the information processing terminal 300 includes, for example, an input operating section 310, a display section (exercise information providing section) 320, a storage section 340, a control section (a correction coefficient setting section, a correction stride acquiring section, and an exercise information providing section) 360, and a communication I/F section 370, as depicted in FIG. 2C.

The input operating section 310 is input means such as a keyboard, a mouse, a touchpad, or a touch panel annexed to the information processing terminal 300.

This input operating section 310 is used for various input operations which are performed when map data is acquired or read, when a movement route (course) during a moving exercise is inputted onto a map, when a movement route inputted onto a map is matched with a provisional movement trajectory (movement route), and when an arbitrary movement section in a movement route on a map is designated.

The display section 320 displays at least information regarding an input operation by the input operating section 310, a map including a movement trajectory generated by the control section 360, exercise information (such as a pitch, a moving speed (running speed), and a stride for each movement section) associated with the map, and the like in a predetermined form.

The storage section 340 stores, in a predetermined storage area, sensor data received from the sensor device 100 via the communication I/F section 370 described below, a provisional movement trajectory, and the like.

Also, by the user US operating the input operating section 310, the storage section 340 stores, in a predetermined storage area, map data including a route of movement during a moving exercise acquired via a site on a network which provides map information service, a storage medium where map information has been recorded, or the like.

Also, the storage section 340 stores data for use or generated when the control section 360 described below executes a predetermined control program or an algorithm program so as to match a provisional movement trajectory with a map, acquires exercise information for each movement section, displays the exercise information on the display section 320 in association with the map, and the like.

The control section 360 is an arithmetic processing unit as a CPU (Central Processing Unit). By executing a predetermined control program, the control section 360 controls various operations, such as an operation of displaying various data, a provisional movement trajectory, and a map on the display section 320, an operation of storing or reading various data, a provisional movement trajectory, and a map in or from the storage section 340, and an operation for the communication of the communication I/F section 370 described below with the sensor device 100.

This control section 360 inputs a movement route (course) during a moving exercise into a map read out from the storage section 340 by the user US operating the input operating section 310, adjusts a value of a correction coefficient with respect to a provisional moving speed estimated during the moving exercise, and matches a provisional movement trajectory with the inputted course.

Then, by using the correction coefficient adjusted by this matching processing, the control section 360 acquires exercise information (such as a pitch, a moving speed, and a stride) for each movement section of the course.

The communication I/F section 370 receives sensor data, a provisional movement trajectory, and the like transmitted from the sensor device 100.

Also, the communication I/F section 370 acquires map data and the like via a network.

<Exercise Support Method>

Next, a control method for the exercise support device according to the present embodiment (exercise support method) is described with reference to the drawings.

Here, a series of control processing in the sensor device 100 according to the present embodiment is described, which includes processing for collecting sensor data during a moving exercise, processing for generating a provisional movement trajectory, processing for matching with map data (training course), and processing for providing exercise information to the user US.

Figure 3:
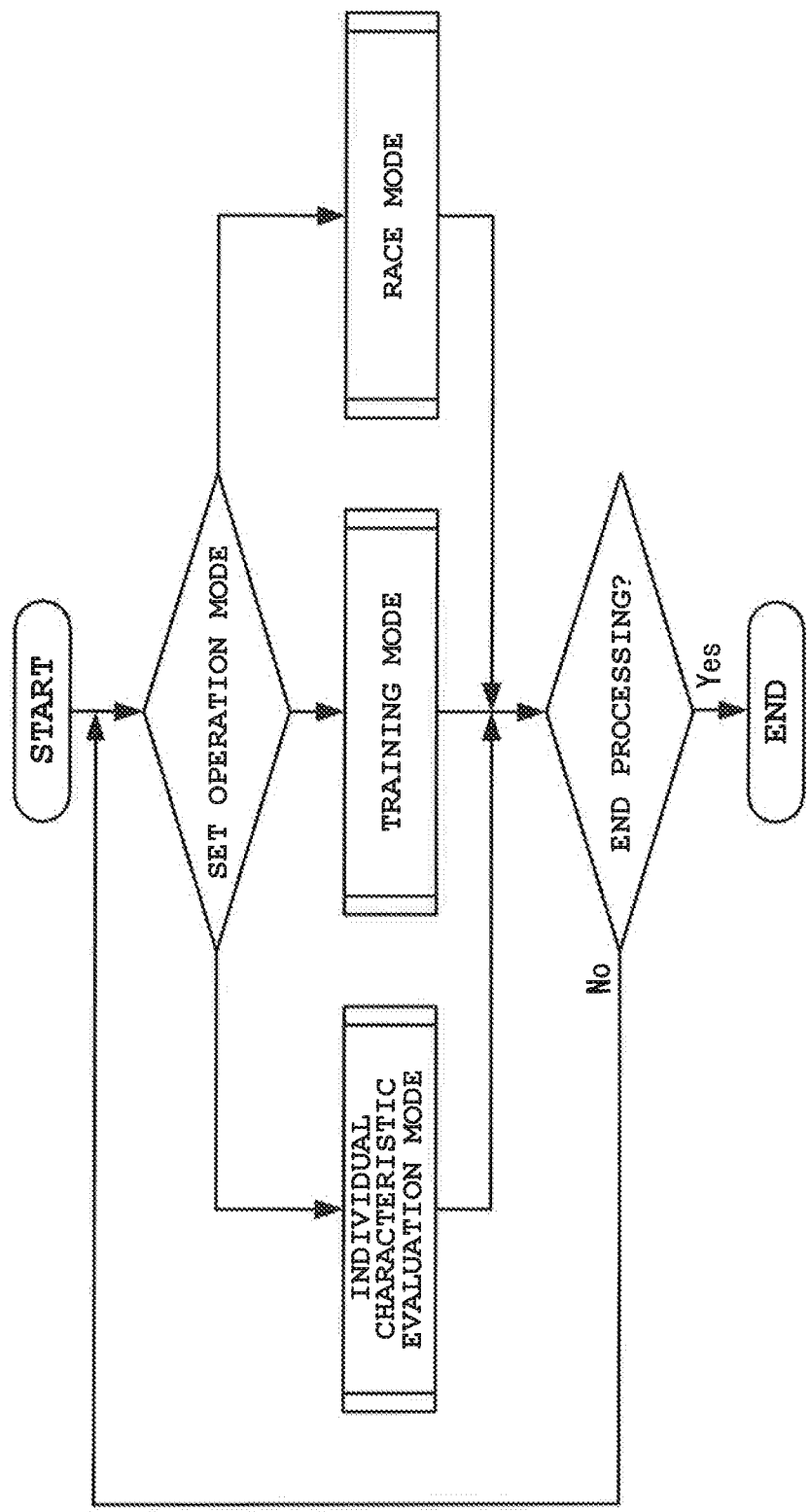
FIG. 3 is a flowchart of an example of a method for controlling the exercise support device according to the embodiment (exercise support method)

FIG. 3 is a flowchart of an example of a method for controlling the exercise support device according to the present embodiment (exercise support method).

Note that the exercise support method described below is achieved based on a predetermined algorithm program executed by a control section of each of the sensor device 100, the wrist device 200, and the information processing terminal 300.

In the exercise support method according to the present embodiment, the user US first sets an operation mode of the exercise support device, as depicted in FIG. 3.

Specifically, the user US operates the input operating section 210 of the wrist device 200 to select an operation mode in the sensor device 100. As a result, a control signal is transmitted from the wrist device 200 via the communication I/F section 170.

Then, the control signal is received by the sensor device 100, and the sensor device 100 is set in the selected operation mode by the control section 160.

In the present embodiment, the operation mode of the exercise support device is selected from among an individual characteristic evaluation mode, a training mode, and a race mode.

Hereinafter, each of these operation modes will be described.

(Individual Characteristic Evaluation Mode)

Figure 4:
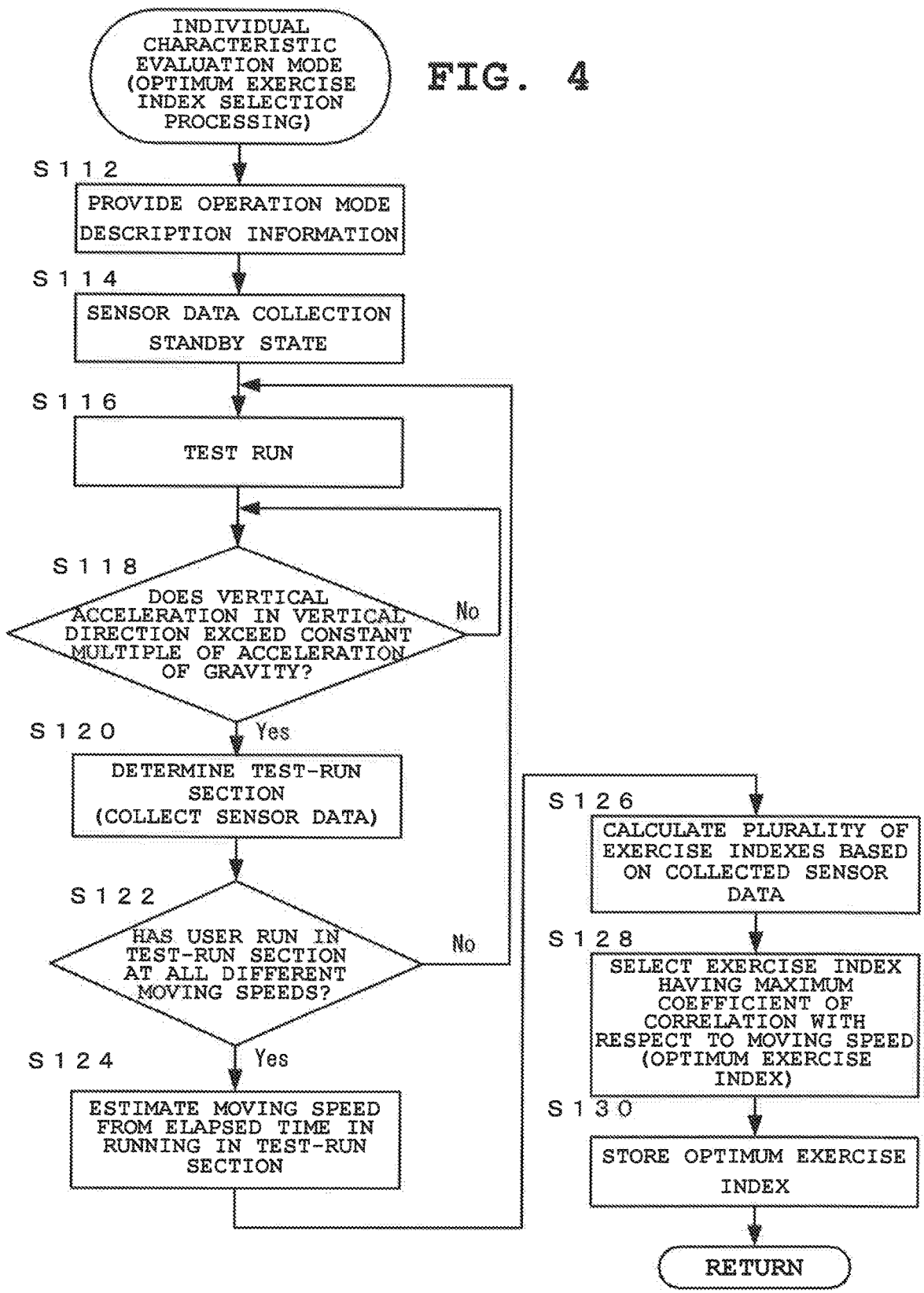
FIG. 4 is a flowchart of an example of control processing that is performed in an individual characteristic evaluation mode in the exercise support method according to the embodiment.

FIG. 4 is a flowchart of an example of control processing that is performed in the individual characteristic evaluation mode in the exercise support method according to the present embodiment.

Figure 5:
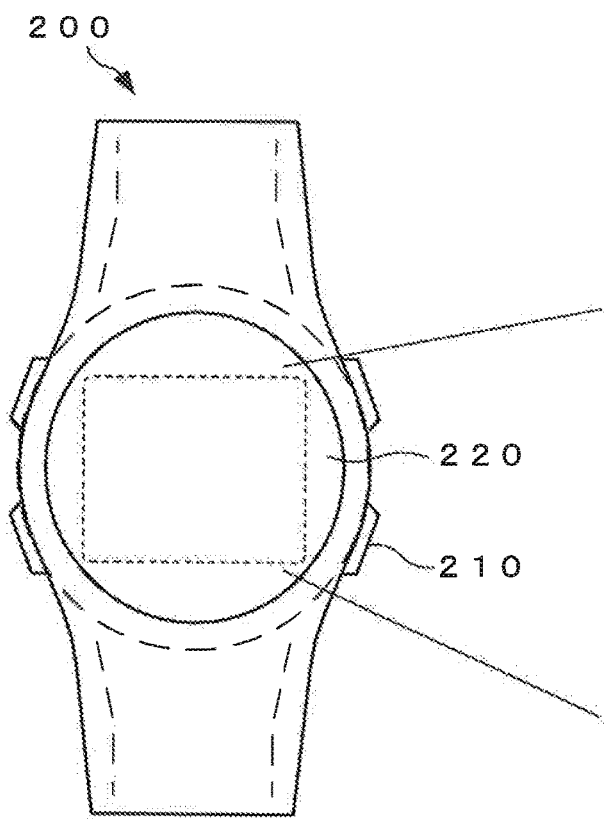
FIG. 5 is a diagram showing an example of description information in the individual characteristic evaluation mode according to the embodiment.

FIG. 5 is a diagram of an example of description information that is displayed on the display section in the individual characteristic evaluation mode according to the present embodiment.

In the individual characteristic evaluation mode, optimum exercise index selection processing is performed in which the individual characteristics of a running motion of the user (exercise characteristics) are evaluated based on sensor data collected during a test run, and a specific exercise index that is optimum for the estimation of a stride of the user US is selected based on the evaluation result.

In the individual characteristic evaluation mode (optimum exercise index selection processing), first, the user US having the sensor device 100 and the wrist device 200 worn on a predetermined part of the body as in FIG. 1 uses the input operating section 210 of the wrist device 200 to select the individual characteristic evaluation mode, as depicted in the flowchart of FIG. 4. As a result, description information regarding this operation mode is provided to the user US (Step S112).

Specifically, character information and image information indicating the start of a series of processing related to the individual characteristic evaluation mode and its specific procedure are displayed on the display section 220 of the wrist device 200 by a predetermined method by which they are visually recognized by the user US sufficiently, such as collective display, roll-up display, or slide display, as depicted in FIG. 5.

Note that the method of providing the description information to the user US is not limited to the display of the character information and the image information on the display section 220 described above. For example, in addition to or in place of the above-described display of the character information and the image information, audio information of contents equivalent to the above-described character information may be outputted from a loudspeaker to be provided to the user US.

Then, a control signal for setting the sensor device 100 in the individual characteristic evaluation mode (a mode setting signal) is transmitted from the wrist device 200 to the sensor device 100.

When the control signal (mode setting signal) is received from the wrist device 200, the sensor device 100 is set in the individual characteristic evaluation mode, and the control section 260 causes the acceleration measuring section 110 and the angular velocity measuring section 120 to start sensing operation, and proceeds to a standby state where it waits for the collection of sensor data (Step S114).

Next, based on the description information, the user US runs (moves)) on a test-run section (movement section) set, for example, from one end to another end of a park at three different moving speeds which are a slow moving speed, a normal moving speed, and a fast moving speed for the user US (Step S116 and Step S122).

Here, in the individual characteristic evaluation mode, a test-run section of, for example, 50 meters is set, and sensor data (acceleration data and angular velocity data) when the user US runs a plurality of times at different moving speeds are collected.

Note that the distance of the test-run section is not necessarily required to be known as long as distances when the user US runs at different moving speeds are substantially the same.

Here, the control section 160 of the sensor device 100 worn on the lumbar part judges whether an acceleration component in the vertical direction collected during the test run exceeds a predetermined constant multiple of gravity acceleration (Step 118).

Then, when judged that the acceleration component in the vertical direction exceeds the predetermined constant multiple of gravity acceleration (YES at Step S118) the control section 160 determines a movement section (Step S120).

In the judgment processing at this Step S118, the constant is set at 2.

Specifically, the control section 160 judges whether a maximum value of the acceleration component in the vertical direction in a period for one footstep among the acceleration data measured by the acceleration measuring section 110 and axially corrected by the axis correcting section 130 exceeds the constant multiple of gravity acceleration which is, for example, twice as much as gravity acceleration.

When operation continues with the maximum value of the acceleration component in the vertical direction in the period for one footstep exceeding the constant multiple of gravity acceleration, the control section 160 judges a section where the acceleration component in the vertical direction is in this state as a movement section.

Then, the control section 160 causes the sensor device 100 to shift from the standby state to a collection state for sensor data collection, and thereby collects sensor data (acceleration data and angular velocity data) outputted from the acceleration measuring section 110 and the angular velocity measuring section 120 at the movement section. Then, after the collected sensor data is axially corrected by the axis correcting section 130, the control section 160 stores the axially-collected sensor data in a predetermined storage area of the storage section 140.

Here, in the movement section determination method at Steps S118 and S120 described above, even when the user US has run in a test-run section of a predetermined distance in each running, there may be a movement section in which the user US is not in a predetermined running state at the start or end of running, and the actual movement section may be slightly different from the distance of the test-run section. However, when the distance of the test-run section is set to, for example, 50 meters, the influence of the difference between the test-run section and the actual movement section with respect to the distance of the test-run section can be normally made relatively small. On the other hand, if the distance of the test-run section is too shorter than the above distance, the influence of the difference between the test-run section and the actual movement section with respect to the distance of the test-run section may be relatively increased. Moreover, if the distance of the test-run section is longer than the above distance, running a plurality of times (here, three times) at different moving speeds may put a heavy burden on the user US. Therefore, the test-run section should preferably be set to about 50 meters in practice.

Note that the distance of the test-run section described herein is merely an example and is not limited thereto. The distance of the test-run section may be set as appropriate based on the physical power, physical condition, and the like of the user US.

Next, based on the time spent by the user US to run the above-described test-run section at different moving speeds, the control section 160 estimates a (ratio of) moving speed (Step S124). Here, a ratio of each moving speed is calculated from each required time on an assumption that the running distance at each test run is the same.

Next, based on the collected sensor data (acceleration data and angular velocity data), the control section 160 acquires a plurality of exercise indexes for use in estimating a stride and a movement distance (running distance) (Step S126).

For example, six exercise indexes IDa to IDf are acquired as exercise indexes in the present embodiment, IDa: a maximum value of a vertical movement of the body of the user in one cycle in running motions IDb: an average value of the square of acceleration in one cycle (acceleration impulse)

IDc: an average value of the square of a component of acceleration in a traveling direction in one cycle (forward direction impulse)

IDd: a value of a landing period of a leg of the user

IDe: a maximum value of a swing angle around the vertical axis of the body of the user in one cycle (pelvis swing angle/yaw)

IDf: a maximum value of a swing angle around an axis laterally penetrating through the body of the user in one cycle (pelvis swing angle/pitch)

Here, one cycle in running motions is, for example, a period of time for two footsteps from when the right leg is landed until when the right leg is landed again after the left leg is landed.

The maximum value of the vertical movement is a difference acquired by calculating a height by integrating acceleration in the vertical direction twice and subtracting a lowest value from a highest value in one cycle.

The landing period is estimated based on acceleration in a front-and-back direction. Specifically, in a running motion, a sharp peak of acceleration in the front-and-back direction appears in a direction (back direction) opposite to the traveling direction at the time of leg landing. Accordingly, timing when a sharp peak in acceleration in the front-and-back direction appears is detected, and judged as landing timing (start timing of the landing period).

Then, the acceleration in the front-and-back direction is reversed from the back direction (at the time of landing) to the front direction during the landing period, and then attenuated. That is, a momentum disappears when a leg takes off the ground, and the acceleration in the front-and-back direction becomes zero. As a result, timing when the acceleration in the front-and-back direction becomes zero is detected, and judged as take-off timing (end timing of the landing period).

An elapsed time from the landing time to the take-off time detected as described above is determined as a landing period.

Next, the control section 160 calculates a value of a coefficient of correlation of each exercise index with respect to the running speed. This coefficient of correlation represents a degree of variations from a straight line of a linear function representing each exercise index with the running speed as a variable.

Then, the control section 160 selects an exercise index with a maximum coefficient of correlation (that is, an exercise index with a maximum coefficient of correlation with respect to the running speed), and takes this exercise index as an optimum exercise index (Val) for estimating a stride during the running (Step S128).

Then, the control section 160 stores the selected optimum exercise index in a predetermined storage area of the storage section 140 (Step S130).

Here, by using the selected optimum exercise index (Val), the moving speed (running speed) can be estimated by approximation with an approximate expression by a linear function with the moving speed as a variable, as represented by the following Equation (1). Here, a and b each represent a predetermined coefficient.

$$\text{Moving speed} = a \times Val + b \quad (1)$$

In the present embodiment, approximation is made by using a linear expression. However, approximation can be made by using a quadratic or tertiary expression.

In a case where the order of the expression is increased, the data amount is preferably large.

The movement distance (running distance) has a relation represented by the following Equation (2) with respect to the moving speed and the movement time.

$$\text{Movement distance} = \text{Moving speed} \times \text{Movement time} \quad (2)$$

The stride has a relation represented by the following Equation (3) with respect to the movement distance and footsteps.

$$\text{Stride} = \text{Movement distance}/\text{footsteps} \quad (3)$$

From Equations (2) and (3) above, the stride has a relation represented by the following Equation (4).

$$\text{Stride} = (a \times Val + b) \times \text{movement time}/\text{footsteps} \quad (4)$$

From the relation of Equation (4), an exercise index with strong correlation with the stride can be said to have strong correlation also with the moving speed (running speed).

Therefore, among the exercise indexes IDa to IDf in the individual characteristic evaluation mode according to the present embodiment, an exercise index with strong correlation with the running speed can be used as the optimum exercise index (Val) for stride estimation.

Here, in the present embodiment, the series of processing is performed in the above-described individual characteristic evaluation mode based on the fact that the exercise index with strong correlation with the moving speed (running speed) closely associated with the stride can be used in order to estimate the stride, as represented in the above-described Equations (1) to (4).

As a result of this configuration, in the present embodiment, an exercise index suitable for stride estimation is judged for each user US by using only sensor data (acceleration data and angular velocity data) outputted from the motion sensor included in the sensor device 100.

FIG. 6A to FIG. 6F are graphs of examples of measurement in the individual characteristic evaluation mode according to the present embodiment, which show a correlation between moving speed and respective exercise indexes for runner A serving as the user US.

FIG. 7A to FIG. 7F are graphs of examples of measurement in the individual characteristic evaluation mode according to the present embodiment, which show a correlation between moving speed and respective exercise indexes for runner B serving as the user US who is different from runner A.

FIG. 8A to FIG. 8F are graphs of examples of measurement in the individual characteristic evaluation mode according to the present embodiment, which show a correlation between moving speed and respective exercise indexes for runner C serving as the user US who is different from runner A and runner B.

The horizontal axis of each of the graphs depicted in FIG. 6A to FIG. 8F represents a running speed.

Here, the running speed on the horizontal axis is represented by a relative value with a value acquired in running at the "normal speed" among three different speeds including the slow speed, the normal speed, and the fast speed as 1.

Figure 8A:
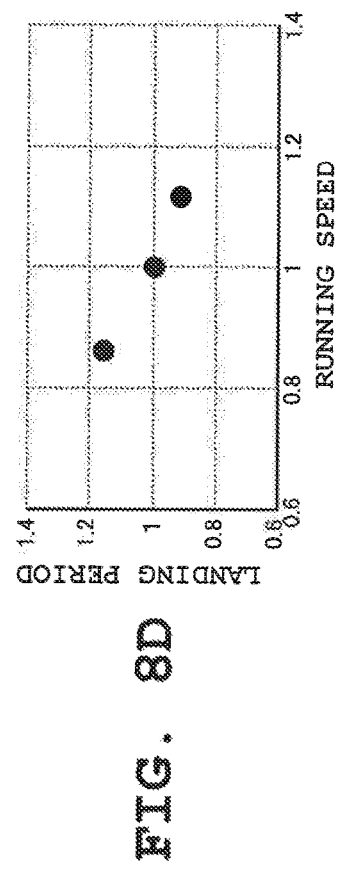
FIG. 8A to FIG. 8F are graphs of examples (correlation between the moving speed and respective exercise indexes of runner C) of measurement in the individual characteristic evaluation mode according to the embodiment.

The vertical axis in FIG. 6A, FIG. 7A, and FIG. 8A represents a maximum vertical movement value in one running cycle serving as an exercise index.

Figure 8B:
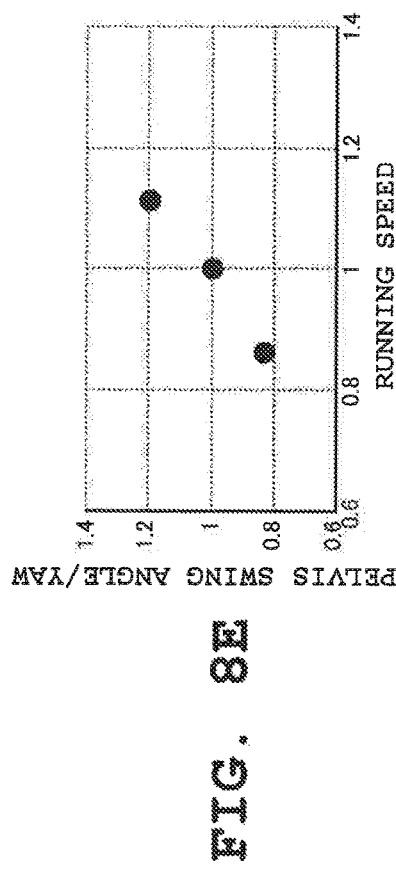

The vertical axis in FIG. 6B, FIG. 7B, and FIG. 8B represents an average value of the squares of acceleration (for vertical components, acceleration of gravity is subtracted) in one cycle serving as an exercise index.

Figure 8C:
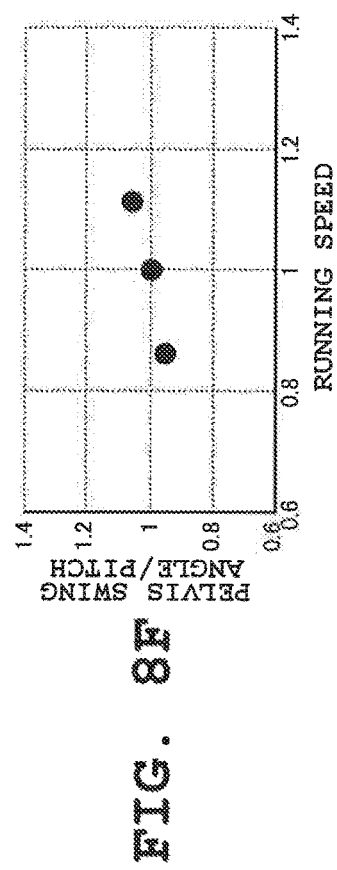

The vertical axis in FIG. 6C, FIG. 7C, and FIG. 8C represents an average value of the squares of forward direction components of acceleration serving as an exercise index.

Figure 8D:
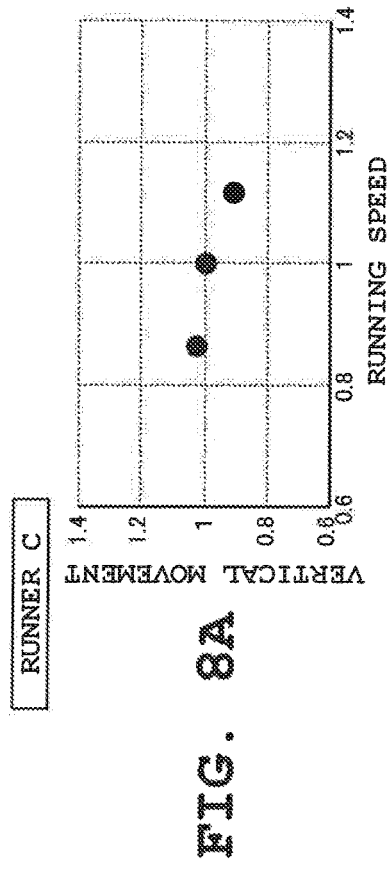
Figure 8E:
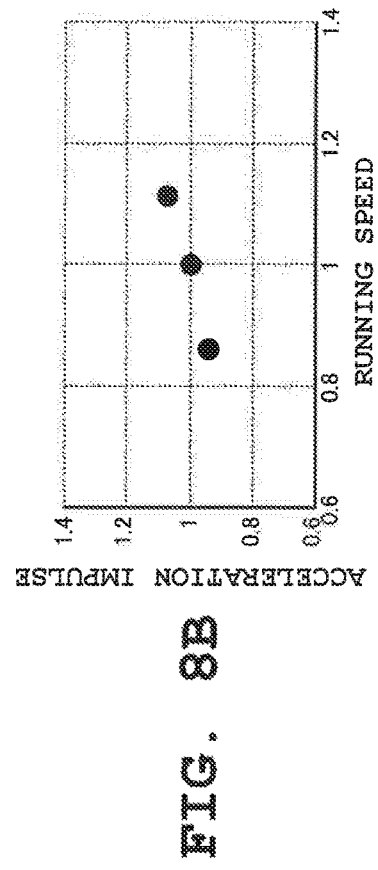
Figure 8F:
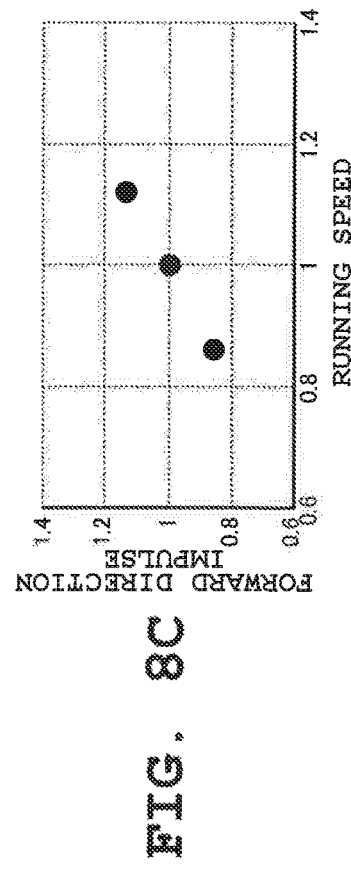

The vertical axis in FIG. 6D, FIG. 7D, and FIG. 8D represents the value of a landing period serving as an exercise index.

The vertical axis in FIG. 6E, FIG. 7E, and FIG. BE represents the value of a maximum swing angle around the vertical axis in one cycle serving as an exercise index.

The vertical axis in FIG. 6F, FIG. 7F, and FIG. BF represents the value of a maximum swing angle around an axis penetrating through the body in one cycle serving as an exercise index.

Here, each value on the vertical axis in FIG. 6A to FIG. 8F is also represented by a relative value with a value acquired in running at the "normal speed" among three different speeds including the slow speed, the normal speed, and the fast speed as 1. These exercise indexes are acquired from sensor data (acceleration data and angular velocity data) outputted from the sensor device 100.

Here, when each of the graphs depicted in FIG. 6A to FIG. 8F is verified, it can be found that the correlation between the running speed on the horizontal axis and the respective exercise indexes set on the vertical axis varies.

In a case where the running speed is estimated from the exercise index on the vertical axis, it is preferable to use the exercise index whose correlation with the running speed is relatively strong and values of which are substantially distributed on a straight line with an absolute value of inclination of points on the graph (exercise index values with respect to the running speed) being on the order of 1.

Here, in the case of runner A, the values of the exercise index depicted in the graph of FIG. 6A (maximum value of vertical movement) are substantially distributed on a straight line with an absolute value of inclination being on the order of 1, and therefore can be judged as suitable as an exercise index for stride estimation. Also, the exercise index depicted in the graph of FIG. 6D (landing period) can be judged as the next suitable exercise index.

In the case of runner B, the values of the exercise index depicted in the graph of FIG. 7C (root mean square of forward acceleration (forward direction impulse)) are substantially distributed on a straight line with an absolute value of inclination being on the order of 1, and therefore can be judged as suitable as an exercise index for stride estimation. Also, the exercise index depicted in the graph of FIG. 7E (maximum swing angle about the vertical axis (pelvis swing angle)) can be judged as the next suitable exercise index.

In the case of runner C, the values of the exercise index depicted in the graph of FIG. 8C (root mean square of forward acceleration (forward direction impulse)) is substantially distributed on a straight line with an absolute value of inclination being on the order of 1, and therefore can be judged as suitable as an exercise index for stride estimation. Also, the exercise index depicted in the graph of FIG. 8D (landing period) and the exercise index depicted in FIG. BE (maximum swing angle about the vertical axis) can be judged as the next suitable exercise indexes.

For each of runners A, B, and C, the exercise index judged as suitable as an exercise index for stride estimation as described above is selected as an optimum exercise index (Val).

Then, by data fitting, values of the coefficients a and b in the above Equation (1) are calculated. Then, the values of the coefficients a and b are stored in a predetermined storage area of the storage section 140 in association with the user US.

As such, in the individual characteristic evaluation mode, the correlation between a running speed and each exercise index is evaluated (or analyzed) based on sensor data collected by test run, whereby a specific exercise index having the strongest correlation with the running speed (optimum exercise index) can be selected as an exercise index for stride estimation, in accordance with the characteristics of the running motion of each user US.

(Training Mode)

Next, the training mode according to the present embodiment is described.

Figure 9A:
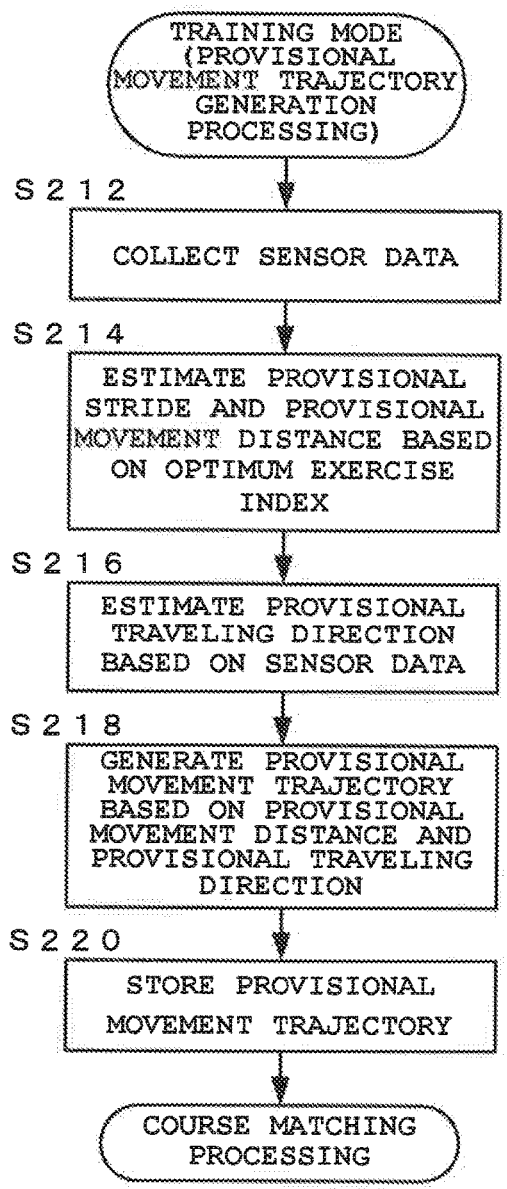
FIG. 9A and FIG. 9B are flowcharts of an example of control processing that is performed in a training mode in the exercise support method according to the embodiment.
Figure 9B:
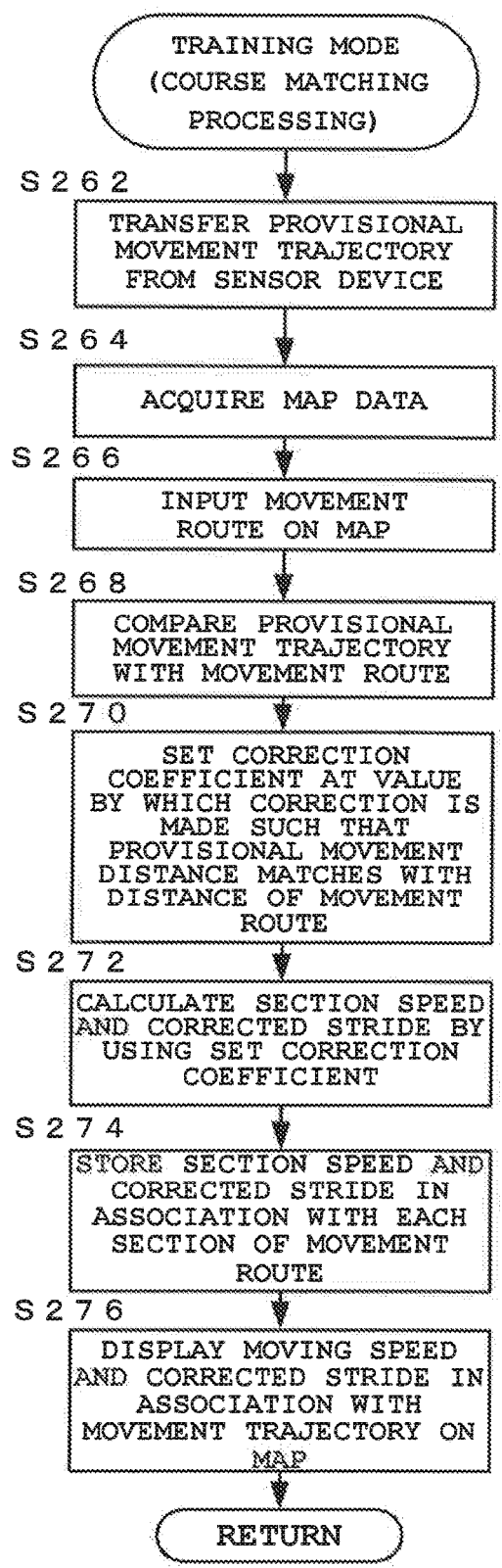

FIG. 9A and FIG. 9B are flowcharts of an example of control processing that is performed in the training mode in the exercise support method according to the present embodiment. FIG. 9A is a flowchart of an example of provisional movement trajectory generation processing that is performed in the training mode according to the present embodiment, and FIG. 9B is a flowchart of course matching processing that is performed in the training mode according to the present embodiment.

Figure 10A:
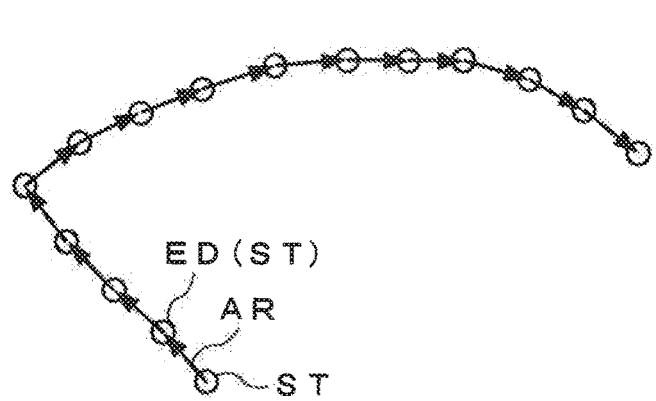
FIG. 10A and FIG. 10B are conceptual diagrams for describing provisional movement trajectory generation processing according to the embodiment.
Figure 10B:
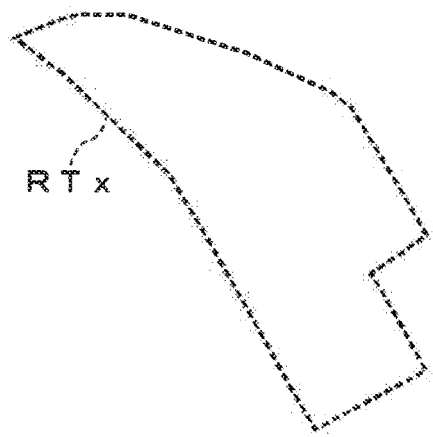

FIG. 10A and FIG. 10B are conceptual diagrams for describing the provisional movement trajectory generation processing according to the present embodiment.

Figure 11A:
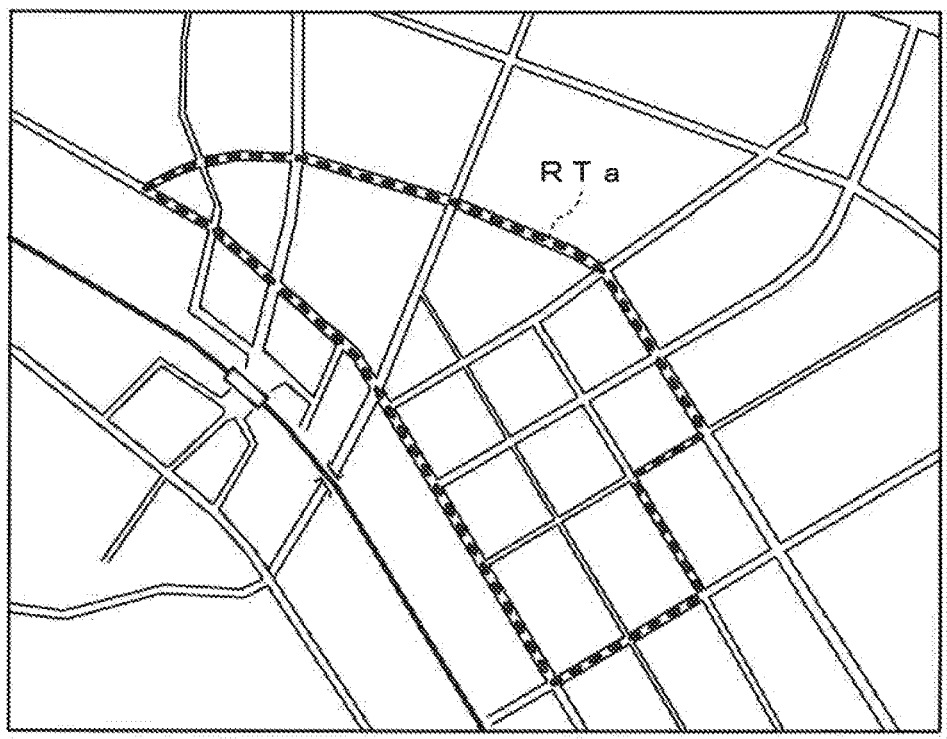
FIG. 11A and FIG. 11B are conceptual diagrams for describing course matching processing according to the embodiment.
Figure 11B:
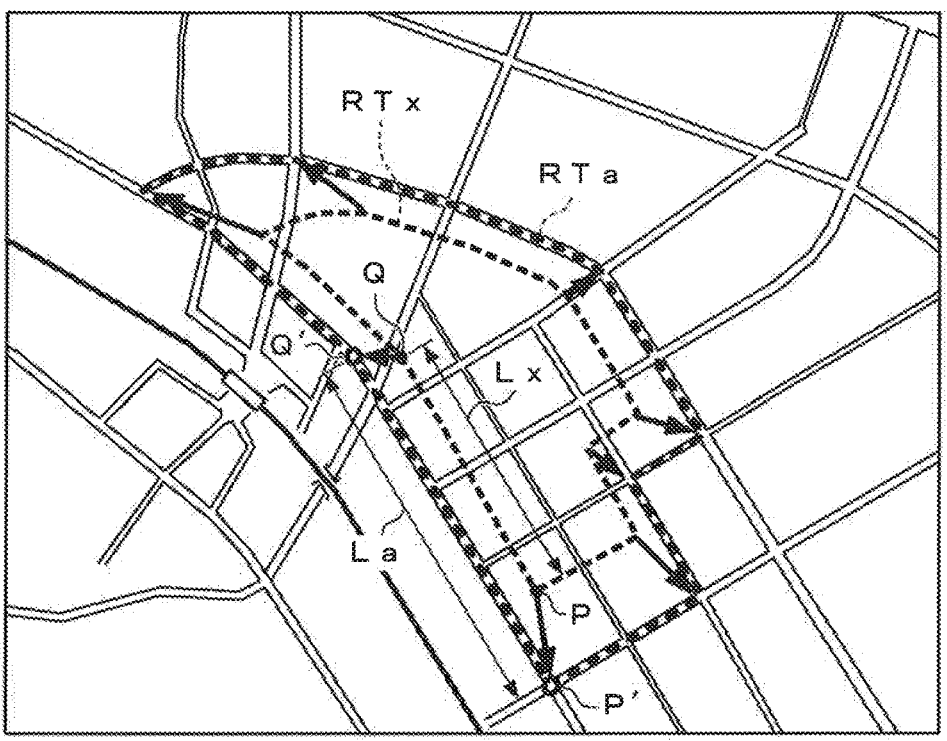

FIG. 11A and FIG. 11B are conceptual diagrams for describing course matching processing according to the present embodiment.

In the training mode, provisional movement trajectory generation processing for generating a provisional movement trajectory based on sensor data collected during training and the optimum exercise index determined in the above-described individual characteristic evaluation mode (optimum exercise index selection processing), and course matching processing for comparing and matching the generated provisional movement trajectory with a training course designated in a map are preformed.

In the training mode (provisional movement trajectory generation processing), first, the user US having the sensor device 100 and the wrist device 200 worn on predetermined parts of the body as in FIG. 1 selects the training mode by using the wrist device 200.

As a result, a control signal for setting the sensor device 100 in the training mode (mode setting signal) is transmitted from the wrist device 200 to the sensor device 100. When the control signal (mode setting signal) is received from the wrist device 200, the sensor device 100 is set in the training mode.

Then, simultaneously with the start of training (running) or slightly before or after training start timing, the user US gives an instruction to start the collection of sensor data by using the input operating section 210 of the wrist device 200, whereby a control signal (start instruction) is transmitted to the sensor device 100.

When the control signal (start instruction) is received from the wrist device 200, the control section 160 of the sensor device 100 causes the acceleration measuring section 110 and the angular velocity measuring section 120 to start sensing operations, and thereby collect sensor data outputted from the acceleration measuring section 110 and the angular velocity measuring section 120 (Step S212), as depicted in the flowchart of FIG. 9A.

Here, the sensor data (acceleration data and angular velocity data) collected during the training is axially corrected by the axis correcting section 130, and stored in a predetermined storage area of the storage section 140.

Here, in the training mode, sensor data when the user US runs (moves) on a desired course, such as a running track, a running course, or a marathon course in an athletic field or the like, is collected.

Next, the control section 160 calculates and estimates a provisional stride by using the above Equation (4) by using the optimum exercise index (Val) and the coefficients a and b acquired in the above-described individual characteristic evaluation mode and stored in the storage section 140 in association with the user US, a movement time calculated based on the sensor data (cyclic changes of acceleration) collected during the training, and footsteps.

The provisional stride is approximate to an actual stride of the user US as will be described below, and is proportional to the actual stride. However, inmost cases, the provisional stride is different from the actual stride.

The control section 160 estimates a distance calculated by multiplying the estimated provisional stride by the footsteps as a provisional movement distance (Step S214).

In addition, the control section 160 estimates a speed calculated by dividing the provisional movement distance by the movement time as a provisional moving speed.

Then, from among the sensor data collected during the training, the control section 160 calculates an angle by integrating the angular velocity around the vertical axis, integrates the angle, averages the integrated angle for each predetermined movement section (for example, every ten footsteps), and thereby detects a change in the traveling direction so as to estimate the traveling direction as a provisional traveling direction (Step S216).

The provisional stride, provisional movement distance, and provisional traveling direction estimated at Steps S214 and S216 described above are each associated with time data and movement section data, and stored in a predetermined storage area of the storage section 140. Furthermore, the control section 160 transmits the data of the provisional stride, the provisional movement distance, and the like to the wrist device 200 via the communication I/F section 170.

As a result, the wrist device 200 causes the transmitted information such as the provisional stride and the provisional movement distance to be displayed on the display section 220 on a substantially real-time basis in a form of, for example, numerical value information or image information, and thereby provides the information to the user US as exercise information.

Next, the control section 160 generates a provisional movement trajectory (provisional running path) during the training based on the provisional movement distance and the provisional traveling direction described above (Step S218).

Specifically, the control section 160 defines an arbitrary position on a virtual plane (two-dimensional space) as a starting point ST, as depicted in FIG. 10A. Then, on the virtual plane, the control section 160 renders, for each predetermined movement section, an arrow (vector) AR of the provisional movement distance in the provisional traveling direction, defines its end point ED as a new starting point, and then sequentially repeats the same processing. As a result, the route of a movement during the training, that is, a provisional movement trajectory RTx is generated on the virtual plane, as depicted in FIG. 10B. The generated provisional movement trajectory RTX is stored in a predetermined storage area of the storage section 140 (Step S220).

In the training mode, course matching processing is performed thereafter. The course matching processing is processing that is performed by the information processing terminal 300 after the end of the running (movement) in the training.

In the course matching processing, after the end of the running (movement) in the training, the control section 160 first transfers the collected sensor data, the generated provisional movement trajectory, and the like from the sensor device 100 via the communication I/F section 170 to the information processing terminal 300 (Step S262), as depicted in the flowchart of FIG. 9B.

In the information processing terminal 300, the input operating section 310 is operated by the user US, and the control section 360 acquires map data including the running (movement) route (training course) of the user US in this training (Step S264).

Here, the map data may be acquired via a site on the Internet for providing a map information service or from a storage medium or the like where the map information has been recorded.

Then, the sensor data and provisional movement trajectory transferred from the sensor device 100 and the acquired map data are stored in a predetermined storage area of the storage section 340 of the information processing terminal 300.

Next, the user US causes a map including the training course to be displayed on the display section 320 of the information processing terminal 300 based on the map data stored in the storage section 340. Then, by using the input operating section 310, the user US inputs a training course RTa, which is the actual movement route of this case, in the map (Step S266), as depicted in FIG. 11A.

Here, as a method for inputting the training course in the map, a method can be adopted in which a plurality of intersections on the roads on the training course RTa are sequentially designated by using a mouse cursor or the like or a line is drawn for designation so as to trace the training course RTa along the roads on the map.

Next, the control section 360 rotates the provisional movement trajectory RTx generated in the above-described provisional movement trajectory generation processing (Steps S212 to S220) and the training course RTa inputted in the map by the user US such that the orientation of the provisional movement trajectory RTx matches with the orientation of the training course RTa, and compares the size of both in accordance with the scale of the map (Step S268).

Then, based on the scale of the map, the control section 360 makes correction by enlargement or reduction such that the distance (provisional movement distance) on the provisional movement trajectory RTx matches with the distance of the training course that is the actual movement route (Step S270), as depicted in FIG. 11B.

Here, the control section 360 calculates and sets a value of a coefficient for correcting the estimated provisional moving speed (hereinafter referred to as "correction coefficient") such that a corresponding point on the provisional movement trajectory RTx matches with a specific point such as a corner where a position on the training course RTa can be identified. By this correction coefficient, the provisional moving speed is corrected, whereby the provisional movement trajectory RTx matches with the training course RTa.

Specifically, point P on the provisional movement trajectory RTx corresponds to specific point P on the training course RTa, and point Q on the provisional movement trajectory RTx corresponds to specific point Q on the training course RTa, as depicted in FIG. 11B.

Then, based on the sensor data collected during the training, a first time point at which the user US is at point P and a second time point at which the user US is at point Q on the provisional movement trajectory RTx are acquired, and a time difference between the first time point and the second time point is acquired as a movement time between point P and point Q.

Next, a provisional movement distance Lx between point P and point Q on the provisional movement trajectory RTx is calculated.

Here, the provisional movement distance Lx has a relation represented by the following Equation (5).

$$Lx=(a \times Val+b) \times \text{Movement time} \quad (5)$$

Here, when an actual distance between point P' and point Q' on the training course RTa is La, a correction coefficient K is acquired by dividing the distance La by the provisional movement distance Lx.

That is, the distance La has a relation represented by the following Equation (6).

$$La=K \times Lx \quad (6)$$

As a result, the above-described coefficients a and b are corrected as represented by the following Equation (7).

$$a'=K \times a, b'=K \times b \quad (7)$$

The correction coefficient K set by the matching of the provisional movement distance Lx is stored in a predetermined storage area of the storage section 140.

Here, when the user US runs a couple of laps on the same course, an average of a plurality of correction coefficients calculated based on the running time for each lap is used as the correction coefficient K.

In the calculation of the moving speed (running speed), by the weighting of most recently measured data being increased, the characteristics of the current running motion of the user US can be reflected to the correction coefficient.

Next, by using the correction coefficient set at a value for matching the provisional movement trajectory RTx with the training course RTa, the control section 360 calculates a moving speed for each predetermined movement section (for example, every ten footsteps), at the above-described Step S270.

Then, based on the moving speed, the control section 360 calculates a stride acquired by correcting the provisional stride for each movement section (hereinafter referred to as "corrected stride") (Step S272).

The corrected stride has a value approximate to the actual stride of the user US.

The moving speed (section speed) and the corrected stride calculated for each movement section is associated with each corresponding movement section of the training course RTa (that is, the matched provisional movement trajectory RTX) and stored in a predetermined storage area of the storage section 340 (Step S274).

Next, by using the input operating section 310 of the information processing terminal 300, the user US selects an arbitrary training course from training courses stored in the storage section 340. As a result, the control section 360 displays a map on which the training course is clearly indicated on the display section 320.

Then, by the user US designating an arbitrary position or a movement section on the training course on the displayed map by using a mouse cursor or the like, the control section 360 causes the moving speed (section speed) and the corrected stride associated with the position or the movement section, or other data to be displayed on a predetermined display area or a pop-up window of the display section 320 in a form of numerical value information or the like, and thereby provides the data to the user US as exercise information (Step S276).

As described above, in the training mode, a provisional movement trajectory estimated based on sensor data after training is matched with a training course that is an actual movement route, whereby more accurate exercise information is acquired based on a correction coefficient set by the matching, and provided to the user US in a form associated with a map.

As a result, the user US can accurately grasp the exercise status in this training.

Accordingly, the user US can improve the next and the following training based on the exercise status in this training.

(Race Mode)

Next, the race mode according to the present embodiment is described.

Figure 12:
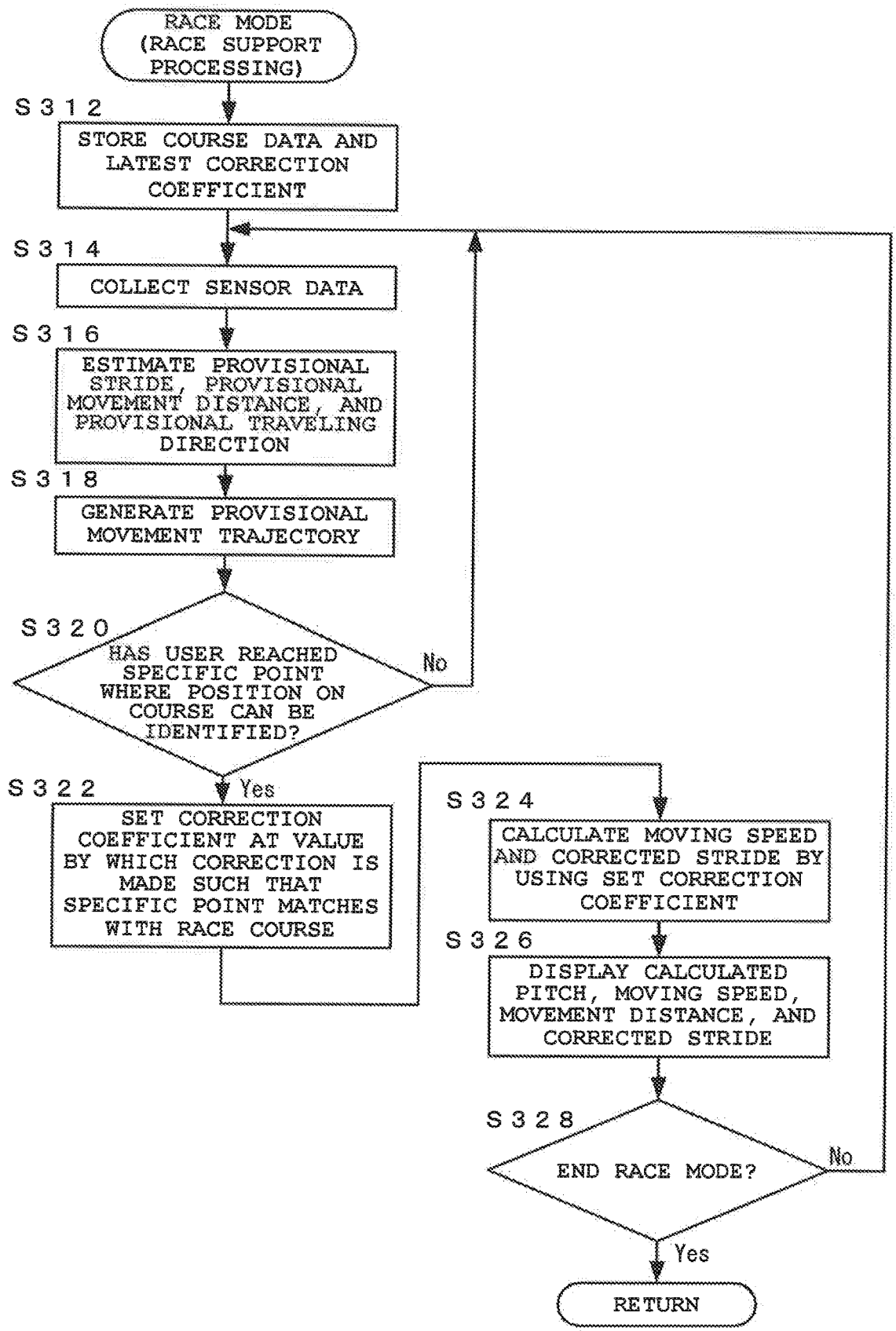
FIG. 12 is a flowchart of an example of control processing that is performed in a race mode in the exercise support method according to the embodiment.

FIG. 12 is a flowchart of an example of control processing that is performed in the race mode in the exercise support method according to the present embodiment.

Figure 13:
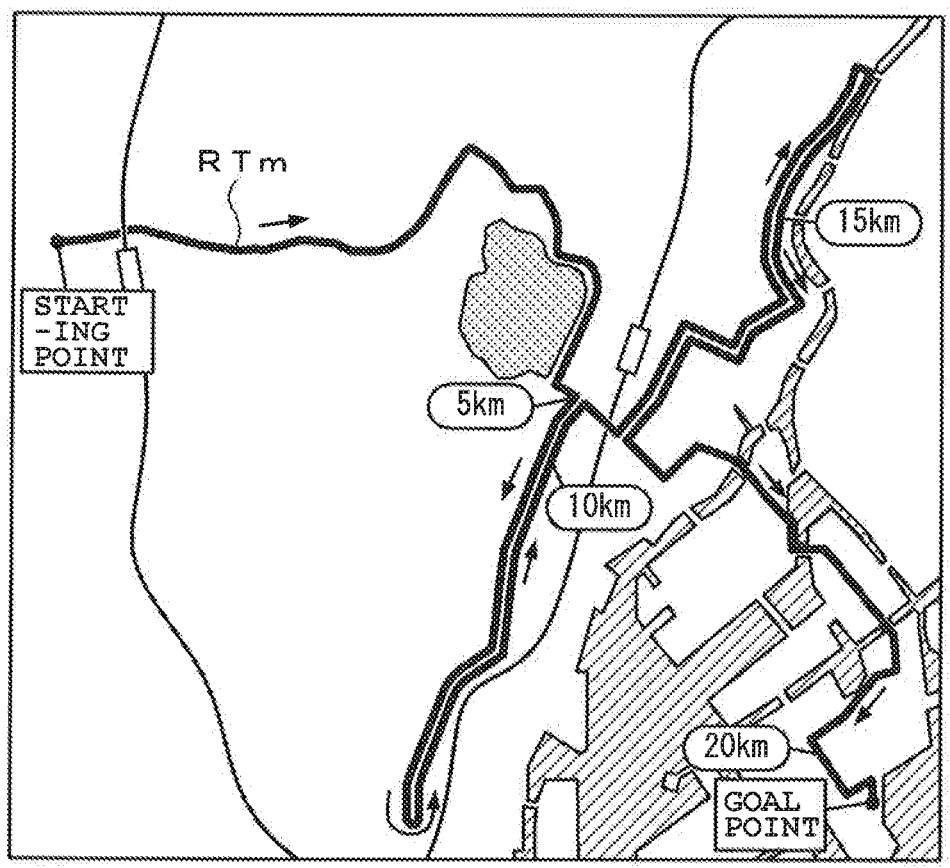
FIG. 13 is a diagram of an example of a race course in the race mode according to the embodiment.

FIG. 13 is a diagram of an example of a race course in the race mode according to the present embodiment.

In the race mode, race support processing is performed in which sensor data collected during running in a race and the value of the correction coefficient set in the training mode described above are adjusted as appropriate and exercise information during the running in the race is acquired based on the adjusted correction coefficient and provided to the user US on a substantially real-time basis.

In the race mode (race support processing) the user US first acquires, for example, the data of a race course RTm as depicted in FIG. 13, and transfers the acquired data together with the latest correction coefficient to the storage section 140 of the sensor device 100 in advance for storage (Step S312), as depicted in the flowchart of FIG. 12. Here, the data of the race course RTm has at least information about the shape and distance of the race course.

Specifically, in a notable marathon race and other races in recent years, the information of the course is published in advance from its race organizer or the like. Thus, the user US can acquire data about the race course RTm from a site of the organizer on the Internet by using, for example, the information processing terminal 300.

Then, the user US reads out the latest correction coefficient stored in the storage section 340 of the information processing terminal 300 as an initial value of the correction coefficient, and transfers the read correction coefficient together with the data of the race course RTm to the sensor device 100.

Here, as an initial value of the correction coefficient, the correction coefficient in the latest or immediately preceding training set in the training mode described above or the correction coefficient set in the latest or immediately preceding race is applied.

Next, the user US having the sensor device 100 and the wrist device 200 worn on predetermined parts of the body selects the race mode by using the wrist device 200, as depicted in FIG. 1.

As a result, a control signal for setting the sensor device 100 in the race mode (mode setting signal) is transmitted from the wrist device 200 to the sensor device 100.

Then, simultaneously with the start of the race or slightly before or after race start timing, the user US gives an instruction to start the collection of sensor data by using the wrist device 200, and thereby transmits a control signal (start instruction) to the sensor device 100.

As a result, the acceleration measuring section 110 and the angular velocity measuring section 120 of the sensor device 100 start sensing operations so as to start the collection of sensor data (Step S314).

The sensor data (acceleration data and angular velocity data) collected during running in the race is axially corrected by the axis correcting section 130 and stored in a predetermined storage area of the storage section 140.

Next, the control section 160 estimates a provisional stride, a provisional movement distance, a provisional moving speed, and a provisional traveling direction based on the optimum exercise index (Val) acquired by the control section 160 in the above-described individual characteristic evaluation mode and the sensor data collected during the running in the race (Step S316).

Then, based on the provisional movement distance and the provisional traveling direction, the control section 160 sequentially generates a provisional movement trajectory during the running in the race (Step S318).

These pieces of data are associated with time data and section data and stored in a predetermined storage area of the storage section 140. In addition, the control section 160 transmits the data to the wrist device 200.

As a result, the wrist device 200 displays the transmitted information related to the provisional stride, the provisional movement distance, the provisional moving speed, the provisional traveling direction, the provisional movement trajectory, and the like on the display section 220 on a substantially real-time basis in a form of, for example, numerical value information or image information, and thereby provides the information to the user US as exercise information.

Note that the processing for estimating various data is achieved by the control section 160 performing processing equivalent to the provisional movement trajectory generation processing (Steps S214 to S218) performed in the above-described training mode.

Next, based on the provisional movement distance and the provisional traveling direction, the control section 160 judges whether the user US has reached a specific point where a position on the race course RTm can be identified, such as a corner (a curve point) (Step S320).

Then, when judged that the user US has reached a specific point where a position on the race course RTm can be identified (YES at Step S320), the control section 160 adjusts the value of the correction coefficient such that the provisional movement trajectory sequentially generated during the running in the race matches with the specific point on the race course RTm (Step S322).

The adjusted new correction coefficient is stored in a predetermined storage area of the storage section 140.

Note that this course matching processing is achieved by the control section 160 performing processing equivalent to the course matching processing performed in the above-described training mode (Steps S268 and S270).

On the other hand, when judged that the user US has not reached a specific point where the course can be identified (NO at Step S320), the control section 160 returns to Step S314 to repeatedly perform the collection of sensor data, the estimation of various data related to the exercise status, and the generation of a provisional movement trajectory.

Next, by using the new correction coefficient adjusted at Step S322 or a weight average value of the correction coefficient and a correction coefficient acquired in the latest training, the control section 160 calculates a moving speed at the present moment.

Subsequently, based on the calculated moving speed and the spent time, the control section 160 calculates a current movement distance. Then, based on footsteps (pitch) per unit time calculated based on the sensor data collected during the running in the race and the moving speed, the control section 160 calculates a corrected stride at the present moment (Step S324).

The calculated pitch, moving speed, movement distance, and corrected stride are transmitted to the wrist device 200.

As a result, the control section 260 of the wrist device 200 displays the transmitted information related to the calculated pitch, moving speed, movement distance, corrected stride, and the like on the display section 220 on a substantially real-time basis in a form of, for example, numerical value information or image information, and thereby provides the information to the user US as exercise information (Step S326).

That is, in this display, the user US is provided with appropriate exercise information where the data in the race course at the present moment and the exercise status of the user US have been reflected more correctly as compared to the initial pitch, moving speed, and stride estimated based on the optimum exercise index (Val) acquired in the individual characteristic evaluation mode and the sensor data collected during the running in the race.

In the above description, the calculated pitch, moving speed, movement distance, and corrected stride are displayed on the display section 220 as exercise information. However, in a case where target values for these items have been set in advance, the calculated values may be compared with the respective target values to indicate differences in value with respect to the respective target values, the change tendency of an increase or a decrease with respect to the target values, or the like, and an improvement-required point for the running status may be displayed such that it is easily recognizable by the user US so as to encourage the user US to improve it.

This series of processing (Steps S314 to S326) is repeatedly performed until the user US ends running in the race course and the collection of sensor data is ended (that is, until the race mode is ended) (Step S328).

As described above, in the race mode, every time the user US reaches a specific point where a course can be identified, the correction coefficient is adjusted (updated), and a provisional movement trajectory to this point generated during the running in the race is matched with the race course.

As a result, the data of a pitch, provisional moving speed, provisional stride, provisional movement distance, and the like estimated based on sensor data collected during the running in the race are corrected as necessary to appropriate data where the current exercise status of the user US have been more correctly reflected, and provided to the user US on a substantially real-time basis.

Accordingly, the user US can appropriately grasp the exercise status on a substantially real-time basis during running in the race, and therefore it is possible to recognize a problem in the exercise status during running in the race and solve the problem to improve a running record.

In the above-described race mode, a corner in a race course is used as a specific point where a position in the race course can be identified when the course matching processing is performed during running in the race. However, the present embodiment is not limited thereto.

For example, in a marathon race or the like, a water station is often installed at some midpoint of the course. At the water station, the user US performs a specific motion for receiving water supply. Accordingly, a configuration may be adopted in which the user US is judged be at the water station when the specific motion is detected, and the course matching processing is performed such that the provisional movement trajectory matches the position of the water station.

Specifically, when receiving a cup or bottle of drink or the like during running, the user US generally performs a water-supply receiving motion of once going out of the course (for example, moves over to the left end of the road) and then soon returning to the original course position. Here, in general, the pitch is slightly decreased during this motion. Thus, a method can be adopted in which a change in the motion status (that is, the bend of the provisional movement trajectory, such as a change in angular velocity around the vertical axis, or the like) is detected by the acceleration measuring section 110 and the angular velocity measuring section 120 of the sensor device 100 and the course matching processing with respect to the water station is performed.

Next, after the end of the race, the control section 160 transfers the sensor data collected during the running in the race, the calculated various data, the correction coefficient used in the course matching processing, and the like from the sensor device 100 via the communication I/F section 170 to the information processing terminal 300.

Then, by the user US using the input operating section 310 of the information processing terminal 300 to acquire lap time data (record information) indicating a transit time for each predetermined distance in the present race which has been published on the Internet or the like, the information processing terminal 300 can perform more detailed analysis after the race.

As described above, in the present embodiment, a corner or the like is used as a point where the course can be identified when the course matching is performed.

On the other hand, in general, a lap time measurement point is often provided on a straight course.

Thus, by obtaining a transit time of the lap time measurement point, a space between corners can be divided for analysis.

In the following descriptions, an example thereof is described using specific numerical values.

In this example, the transit time at 5 km is 25 minutes 10 seconds.

Also, preceding and subsequent corners for use in the course matching are at a point of 2 km and a point of 8.5 km, respectively, and transit times measured by the sensor are 11 minutes 30 seconds and 42 minutes 30 seconds.

Accordingly, it can be found that a time spent for 3 km between the point of 2 km to the point of 5 km is 13 minutes 50 seconds, and an average speed in this movement section acquired by diving the movement section distance by the spend time is 3.61 m/second.

Also, it can be found that a time spent for 3.5 km between the point of 5 km and the point of 8.5 km is 17 minutes 20 seconds, and an average speed in this movement section acquired by dividing the movement section distance by the spent time is 3.37 second.

By using information at lap time measurement points provided on a race course as described above, movement sections can be further divided and speed information in each movement section can be acquired.

As a result, the correction coefficient and the exercise information are complemented in more detail, and exercise information with more accurate numerical values can be provided. Therefore, the user US can accurately grasp the exercise status at the time of racing and utilize it in the next race and training.

In the present embodiment, various data such as a pitch, a moving speed, a stride, and the like during exercise can be accurately estimated and provided to the user US based on sensor data (acceleration data and angular velocity data) collected by the motion sensor, without using measurement data by GPS.

Therefore, even in an area between urban buildings where GPS radio waves are difficult to receive, the exercise status can be accurately grasped and utilized for the judgment and improvement of the exercise status.

In the present embodiment, a moving speed is estimated by a linear expression using only one optimum exercise index. However, the present invention is not limited thereto. This moving speed may be estimated by a quadratic expression and a tertiary expression by also using exercise indexes that are second and third suitable.

Modification Example

Figure 14:
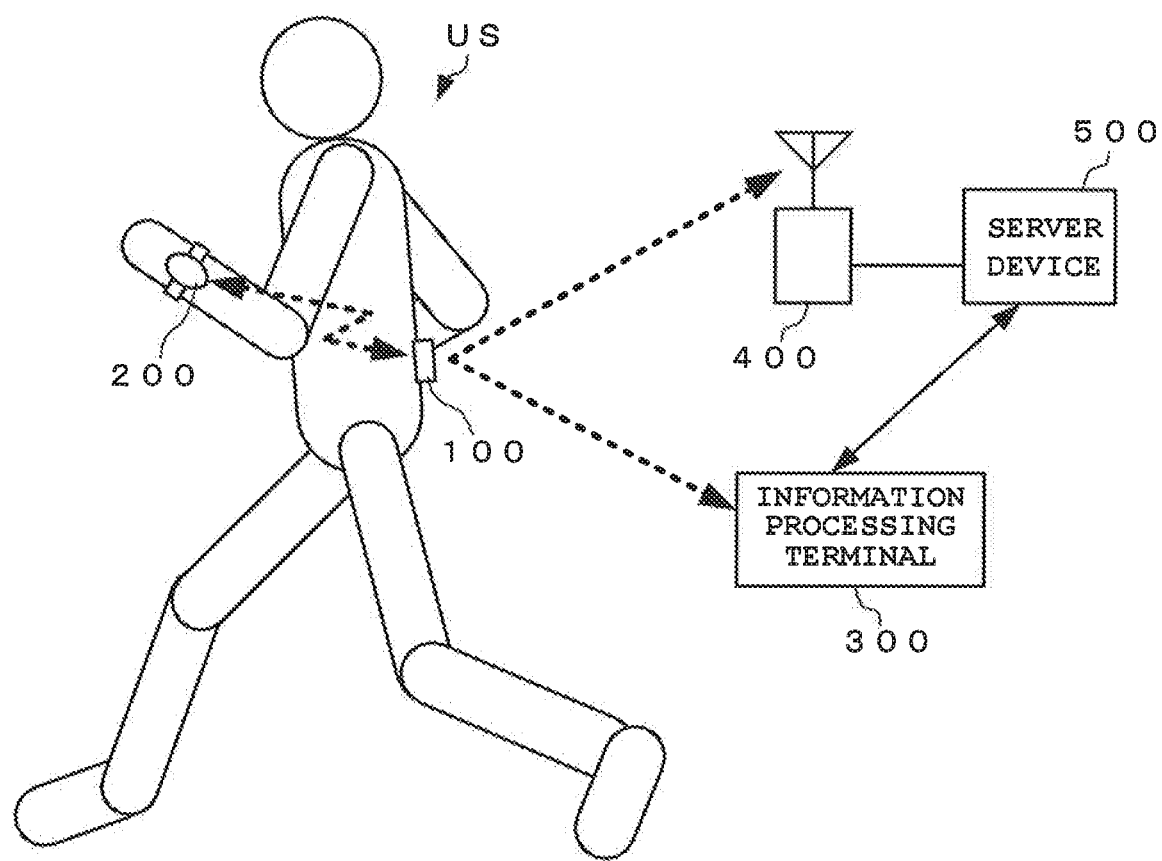
FIG. 14 is a schematic structural diagram of a modification example of the exercise support device according to the embodiment.

FIG. 14 is a schematic structural diagram of a modification example of the exercise support device according to the present embodiment.

In the above-described embodiment, the series of processing for the collection of sensor data during exercise, the estimation of various data related to an exercise status, and the generation of a provisional movement trajectory is performed in the sensor device 100. Then, the matching processing for matching the provisional movement trajectory with the course and processing for acquiring and displaying exercise information such as a pitch, moving speed, corrected stride based on the result (the set correction coefficient) are performed in the information processing terminal 300.

However, the present invention is not limited thereto.

For example, the exercise support device may include a server device 500 and a cloud system connected to a network, as depicted in FIG. 14.

Here, sensor data and a provisional movement trajectory transmitted after exercise from the sensor device 100 are transferred via the information processing terminal 300 and a network relay device 400 to the server device 500. Then, in the server device 500, processing such as course matching of the provisional movement trajectory and acquisition of exercise information is performed.

Also, the exercise support device of the present invention having the structure depicted in FIG. 14 may be configured such that only the collection of sensor data is performed during a moving exercise by the sensor device 100.

Then, the collected sensor data is transferred after the moving exercise via the information processing terminal 300 and the network relay device 400 to the server device 500. Subsequently, in the server device 500, processing such as the estimation of various data related to the exercise status, the generation of a provisional movement trajectory, the course matching of the provisional movement trajectory, and the acquisition of exercise information is performed.

In this case, the information processing terminal 300 is only required to have a function for being connected to a network or the server device 500 so as to allow information to be viewed, and therefore may have a simple structure. By accessing the server device 500 by using the information processing terminal 300 having a simple structure, the user US can view exercise information associated with the course in the map.

In the above-described embodiment, when an acceleration rate outputted from the acceleration measuring section 110 is equal to or smaller than a predetermined value at the time of collecting sensor data by the sensor device 100, the control section 160 may judge that the user US is not doing a moving exercise and is at rest. If this rest state continues more than a predetermined time, for example, the control section 160 may stop the operation of collecting sensor data and perform the calibration of the angular velocity measuring section 120.

Also, in the above-described embodiment, the sensor device 100 is worn on the lumbar part of the user US, as depicted in FIG. 1. However, the present invention is not limited thereto.

The sensor device 100 may be worn on any portion as long as it is located along a body axis passing through the center of a human body or on the body trunk. For example, the sensor device 100 may be worn on the chest part, neck part, or abdominal part.

Moreover, the method of wearing the sensor device 100 on a body is not particularly limited.

For example, various wearing methods can be adopted as appropriate, such as a method where the sensor device 100 is clipped to training clothes, a method where the sensor device 100 is attached by a tape member or the like, a method where the sensor device 100 is wound around a body with a belt or the like, or a method where the sensor device 100 is incorporated into clothes.

Here, when the sensor device 100 is worn on a portion on an upper-half body or away from the ground surface, such as the chest part or neck part, a sharp peak of acceleration occurring when a foot is landed is difficult to reach the upper-half body part including the chest and neck, and therefore measurement may be difficult in some cases. In these cases, the landing period among the above-described exercise indexes may be calculated by using another calculation method.

For example, in general, acceleration in the vertical direction is 1 G (9.8 m/s2) when a body weight is supported by a landed foot after foot landing. Then, a behavior is observed in which the acceleration increases with a kick motion and then attenuates. Accordingly, a method may be adopted in which a section where acceleration in the vertical direction exceeds 1 G is detected as a section where a kick motion is actively being performed, and this section is taken as a landing period.

Also, in the above-described embodiment, a distance designated on a map is applied when a correction coefficient is set. However, the present invention is not limited thereto. For example, positioning data by GPS may be used.

Here, a position measured by GPS includes a positioning error of about 10 meters. Therefore, when a speed is estimated based on GPS positioning accuracy for a straight line of about 100 meters, an influence of this positioning error is relatively large at about 10%. However, in the case of a straight line of about 2 kilometers, this influence by a positioning error can be decreased to be equal to or smaller than 1%. Therefore, if the straight line portion of a provisional movement trajectory is sufficiently long and the status of the reception of radio waves from a GPS satellite at both end positions are favorable, the value of the correction coefficient can be adjusted based on distance information acquired by GPS position estimation.

While the present invention has been described with reference to the preferred embodiments, it is intended that the invention be not limited by any of the details of the description therein but includes all the embodiments which fall within the scope of the appended claims.

What is claimed is:

1. An exercise support device comprising:
   a motion sensor which is configured to be worn on a body of a user, the motion sensor detecting acceleration and angular velocity, and the motion sensor outputting sensor data related to a motion status of the body of the user when the user is performing a moving exercise, the sensor data including acceleration data and angular velocity data corresponding to the acceleration and the angular velocity detected by the motion sensor; and
   a hardware processor which, under control of a stored program, acquires exercise information regarding an exercise status of the user, the exercise information including at least one of pitch, moving speed, movement distance, traveling direction, movement trajectory, and stride of the user,
   wherein the hardware processor is selectively operable in each of a first mode and a second mode different from the first mode,
   wherein in the first mode, the hardware processor, under control of the stored program, executes processes comprising:
      acquiring, from the sensor data, a plurality of values for each of a plurality of different exercise indexes, the plurality of values indicating respective values of the exercise index acquired when the user moves by the moving exercise on a same movement section at each of a first moving speed, a second moving speed slower than the first moving speed, and a third moving speed faster than the first moving speed,
      for each of the plurality of different exercise indexes, plotting, on a graph having a first axis representing a moving speed and a second axis representing values of the exercise index, points corresponding to the respective values of the exercise index acquired for the first moving speed, the second moving speed, and the third moving speed, and calculating an absolute value of an inclination of a straight line connecting the plotted points,
      selecting one of the plurality of different exercise indexes as a specific exercise index, the specific exercise index being an exercise index having a strongest correlation with moving speed among the plurality of different exercise indexes, and the specific exercise index being selected based on the calculated absolute value of the inclination of the straight line connecting the plotted points on the graph plotted therefor, and calculating a coefficient that is used in an approximate expression which represents the specific exercise index and is a linear function including the moving speed as a variable and the coefficient, wherein in the second mode, the hardware processor, under control of the stored program, acquires the exercise information based on (i) the sensor data acquired when the user moves on a movement route different from the movement section by the moving exercise, (ii) the specific exercise index selected in the first mode, and (iii) the coefficient calculated in the first mode, wherein the plurality of different exercise indexes include:

(i) a maximum value of a vertical movement of the body of the user in one cycle of the moving exercise, (ii) an average value of a square of the acceleration in one cycle of the moving exercise, (iii) an average value of a square of a traveling direction component of the acceleration in one cycle of the moving exercise, (iv) a value of a landing period of a foot of the user in the moving exercise, (v) a maximum value of a swing angle around a vertical axis of the body of the user in one cycle of the moving exercise, and (vi) a maximum value of a swing angle around an axis laterally penetrating through the body of the user in one cycle of the moving exercise, and wherein the exercise support device further comprises a display which displays the exercise information acquired in the second mode with the movement route.

2. The exercise support device according to claim 1, wherein the hardware processor acquires, as the exercise information, an estimation value of a stride of the user moving on the movement route by the moving exercise, when the user is performing the moving exercise.

3. The exercise support device according to claim 2, wherein the hardware processor, under control of the stored program, executes further processes comprising:

estimating a provisional stride of the user making a moving motion based on (i) the sensor data outputted from the motion sensor when the user is making the moving motion on the movement route by the moving exercise, (ii) the specific exercise index, and (iii) the coefficient, acquiring a movement time spent by the user to move between two different specific points at which a position of the user on the movement route is identifiable, based on the sensor data, calculating a provisional movement distance that the user is estimated to have moved in the movement time, based on the movement time and the provisional stride, setting a correction coefficient for correcting the provisional movement distance at a value for matching the provisional movement distance after correction with a distance between the two specific points on the movement route, and calculating an estimation value of the stride based on the correction coefficient.

4. The exercise support device according to claim 3, wherein the two specific points are points where the movement route is curved, wherein the angular velocity data indicates an angular velocity of the user around a vertical axis, and wherein the hardware processor detects two clock times at which the user is judged to be at the two specific points on the movement route, based on a change of the angular velocity of the user around the vertical axis detected in the angular velocity data, and acquires the movement time based on the two clock times.

5. The exercise support device according to claim 2, wherein the hardware processor, under control of the stored program, executes further processes comprising:

estimating a provisional stride of the user making a moving motion based on (i) the sensor data outputted from the motion sensor when the user is making the moving motion on the movement route by the moving exercise, (ii) the specific exercise index, and (iii) the coefficient, sequentially generating a movement trajectory of the user moving on the movement route as a provisional movement trajectory based on the provisional stride and the sensor data, when the user is performing the moving exercise, setting a correction coefficient for correcting the provisional movement trajectory at a value by which a correction is made such that the provisional movement trajectory after the correction matches with a specific point where a position of the user on the movement route is identifiable, when the user is judged to have reached the specific point based on the sensor data, and calculating a corrected stride acquired by correcting the provisional stride by the correction coefficient as an estimation value of the stride, when the user is performing the moving exercise.

6. The exercise support device according to claim 5, wherein the specific point is a point where the movement route is curved, wherein the angular velocity data indicates an angular velocity of the user around a vertical axis, and wherein the control section judges whether the user has reached the specific point on the movement route based on a change of the angular velocity of the user around the vertical axis detected in the angular velocity data.

7. The exercise support device according to claim 5, wherein the angular velocity data indicates an angular velocity of the user around a vertical axis, and wherein the control section acquires a provisional traveling direction for finding a traveling direction of the user during the moving exercise, based on an integral value of the angular velocity of the user around the vertical axis in the angular velocity data, and generates the provisional movement trajectory based on the provisional stride and the provisional traveling direction.

8. An exercise support method executed by an exercise support device comprising a motion sensor configured to be worn on a body of a user and a hardware processor that is selectively operable in each of a first mode and a second mode different from the first mode, the method comprising:

acquiring, by the hardware processor operating in the first mode, from sensor data outputted from the motion sensor worn on the body of the user, a plurality of values for each of a plurality of different exercise indexes, the plurality of values indicating respective values of the exercise index acquired when the user moves by a moving exercise on a same movement section at each of a first moving speed, a second moving speed slower than the first moving speed, and a third moving speed faster than the first moving speed, the motion sensor detecting acceleration and angular velocity, and the sensor data including acceleration data and angular velocity data corresponding to the acceleration and the angular velocity detected by the motion sensor;

for each of the plurality of different exercise indexes, plotting, by the hardware processor operating in the first mode, on a graph having a first axis representing a moving speed and a second axis representing values of the exercise index, points corresponding to the respective values of the exercise index acquired for the first moving speed, the second moving speed, and the third moving speed, and calculating an absolute value of an inclination of a straight line connecting the plotted points;

selecting, by the hardware processor operating in the first mode, one of the plurality of different exercise indexes as a specific exercise index, the specific exercise index being an exercise index having a strongest correlation with moving speed among the plurality of different exercise indexes, and the specific exercise index being selected based on the calculated absolute value of the inclination of the straight line connecting the plotted points on the graph plotted therefor;

calculating, by the hardware processor operating in the first mode, a coefficient that is used in an approximate expression which represents the specific exercise index and is a linear function including the moving speed as a variable and the coefficient; and acquiring, by the hardware processor operating in the second mode, exercise information regarding an exercise status of the user based on (i) the sensor data acquired when the user moves on a movement route different from the movement section by the moving exercise, (ii) the specific exercise index selected, and (iii) the coefficient calculated, the exercise information including at least one of pitch, moving speed, movement distance, traveling direction, movement trajectory, and stride of the user, wherein the plurality of different exercise indexes include:
(i) a maximum value of a vertical movement of the body of the user in one cycle of the moving exercise,
(ii) an average value of a square of the acceleration in one cycle of the moving exercise,
(iii) an average value of a square of a traveling direction component of the acceleration in one cycle of the moving exercise,
(iv) a value of a landing period of a foot of the user in the moving exercise,
(v) a maximum value of a swing angle around a vertical axis of the body of the user in one cycle of the moving exercise, and
(vi) a maximum value of a swing angle around an axis laterally penetrating through the body of the user in one cycle of the moving exercise, and wherein the exercise support method further comprises displaying, on a display, the exercise information acquired in the second mode with the movement route.

9. The exercise support method according to claim 8, wherein the exercise information includes an estimation value of a stride of the user moving on the movement route by the moving exercise, when the user is performing the moving exercise.

10. The exercise support method according to claim 9, further comprising:
estimating a provisional stride of the user making a moving motion based on (i) the sensor data outputted from the motion sensor when the user is making the moving motion on the movement route by the moving exercise, (ii) the specific exercise index, and (iii) the coefficient;
acquiring a movement time spent by the user to move between two different specific points at which a position of the user on the movement route is identifiable, based on the sensor data;
calculating a provisional movement distance that the user is estimated to have moved in the movement time, based on the movement time and the provisional stride;
setting a correction coefficient for correcting the provisional movement distance at a value for matching the provisional movement distance after correction with a distance between the two specific points on the movement route; and
calculating an estimation value of the stride based on the correction coefficient.

11. The exercise support method according to claim 9, further comprising:
estimating a provisional stride of the user making a moving motion based on (i) the sensor data outputted from the motion sensor when the user is making the moving motion on the movement route by the moving exercise, (ii) the specific exercise index, and (iii) the coefficient;
sequentially generating a movement trajectory of the user moving on the movement route as a provisional movement trajectory based on the provisional stride and the sensor data, when the user is performing the moving exercise;
setting a correction coefficient for correcting the provisional movement trajectory at a value by which a correction is made such that the provisional movement trajectory after the correction matches with a specific point where a position of the user on the movement route is identifiable, when the user is judged to have reached the specific point based on the sensor data; and
calculating a corrected stride acquired by correcting the provisional stride by the correction coefficient as an estimation value of the stride, when the user is performing the moving exercise.

12. A non-transitory computer-readable storage medium having an exercise support program stored thereon that is executable by a computer to control the computer to execute processes comprising:
acquiring, in a first mode, from sensor data outputted from a motion sensor worn on a body of a user, a plurality of values for each of a plurality of different exercise indexes, the plurality of values indicating respective values of the exercise index acquired when the user moves by a moving exercise on a same movement section at each of a first moving speed, a second moving speed slower than the first moving speed, and a third moving speed faster than the first moving speed, the motion sensor detecting acceleration and angular velocity, and the sensor data including acceleration data and angular velocity data corresponding to the acceleration and the angular velocity detected by the motion sensor;
for each of the plurality of different exercise indexes, plotting, in the first mode, on a graph having a first axis representing a moving speed and a second axis representing values of the exercise index, points corresponding to the respective values of the exercise index acquired for the first moving speed, the second moving speed, and the third moving speed, and calculating an absolute value of an inclination of a straight line connecting the plotted points;

selecting, in the first mode, one of the plurality of different exercise indexes as a specific exercise index, the specific exercise index being an exercise index having a strongest correlation with moving speed among the plurality of different exercise indexes, and the specific exercise index being selected based on the calculated absolute value of the inclination of the straight line connecting the plotted points on the graph plotted therefor;

calculating, in the first mode, a coefficient that is used in an approximate expression which represents the specific exercise index and is a linear function including the moving speed as a variable and the coefficient; and acquiring, in a second mode different from the first mode, exercise information regarding an exercise status of the user based on (i) the sensor data acquired when the user is moving on a movement route different from the movement section by the moving exercise, (ii) the specific exercise index selected, and (iii) the coefficient calculated, the exercise information including at least one of pitch, moving speed, movement distance, traveling direction, movement trajectory, and stride of the user, wherein the plurality of different exercise indexes include:
(i) a maximum value of a vertical movement of the body of the user in one cycle of the moving exercise,
(ii) an average value of a square of the acceleration in one cycle of the moving exercise,
(iii) an average value of a square of a traveling direction component of the acceleration in one cycle of the moving exercise,
(iv) a value of a landing period of a foot of the user in the moving exercise,
(v) a maximum value of a swing angle around a vertical axis of the body of the user in one cycle of the moving exercise, and
(vi) a maximum value of a swing angle around an axis laterally penetrating through the body of the user in one cycle of the moving exercise, and
wherein the program controls the computer to execute a further process comprising displaying, on a display, the exercise information acquired in the second mode with the movement route.

13. The non-transitory computer-readable storage medium according to claim 12, wherein the exercise information includes an estimation value of a stride of the user moving on the movement route by the moving exercise, when the user is performing the moving exercise.

14. The non-transitory computer-readable storage medium according to claim 13, the program controlling the computer to execute further processes comprising:
estimating a provisional stride of the user making a moving motion based on (i) the sensor data outputted from the motion sensor when the user is making the moving motion on the movement route by the moving exercise, (ii) the specific exercise index, and (iii) the coefficient;
acquiring a movement time spent by the user to move between two different specific points at which a position of the user on the movement route is identifiable, based on the sensor data;
calculating a provisional movement distance that the user is estimated to have moved in the movement time, based on the movement time and the provisional stride;
setting a correction coefficient for correcting the provisional movement distance at a value for matching the provisional movement distance after correction with a distance between the two specific points on the movement route; and
calculating an estimation value of the stride based on the correction coefficient.

15. The non-transitory computer-readable storage medium according to claim 13, the program controlling the computer to execute further processes comprising:
estimating a provisional stride of the user making a moving motion based on the sensor data outputted from the motion sensor when the user is making the moving motion on the movement route by the moving exercise, the specific exercise index, and the coefficient;
sequentially generating a movement trajectory of the user moving on the movement route as a provisional movement trajectory based on the provisional stride and the sensor data, when the user is performing the moving exercise;
setting a correction coefficient for correcting the provisional movement trajectory at a value by which a correction is made such that the provisional movement trajectory after the correction matches with a specific point where a position of the user on the movement route is identifiable, when the user is judged to have reached the specific point based on the sensor data; and
calculating a corrected stride acquired by correcting the provisional stride by the correction coefficient as an estimation value of the stride, when the user is performing the moving exercise.

* * * * *